US009695262B2

(12) United States Patent
Mohapatra et al.

(10) Patent No.: US 9,695,262 B2
(45) Date of Patent: Jul. 4, 2017

(54) MOLECULARLY IMPRINTED POLYMERS HAVING AFFINITY FOR NATRIURETIC PEPTIDES

(75) Inventors: Subhra Mohapatra, Lutz, FL (US); Chunyan Wang, Tampa, FL (US)

(73) Assignee: UNIVERSITY OF SOUTH FLORIDA, Tampa, FL (US)

( * ) Notice: Subject to any disclaimer, the term of this patent is extended or adjusted under 35 U.S.C. 154(b) by 0 days.

(21) Appl. No.: 14/000,326

(22) PCT Filed: Feb. 24, 2012

(86) PCT No.: PCT/US2012/026449
§ 371 (c)(1),
(2), (4) Date: Aug. 19, 2013

(87) PCT Pub. No.: WO2012/138429
PCT Pub. Date: Oct. 11, 2012

(65) Prior Publication Data
US 2013/0330384 A1   Dec. 12, 2013

Related U.S. Application Data

(60) Provisional application No. 61/446,739, filed on Feb. 25, 2011.

(51) Int. Cl.
| | |
|---|---|
| C08F 220/06 | (2006.01) |
| C40B 60/12 | (2006.01) |
| C40B 30/04 | (2006.01) |
| G01N 33/74 | (2006.01) |
| B82Y 5/00 | (2011.01) |
| C07K 14/58 | (2006.01) |
| A61K 38/00 | (2006.01) |

(52) U.S. Cl.
CPC .............. *C08F 220/06* (2013.01); *B82Y 5/00* (2013.01); *C07K 14/58* (2013.01); *G01N 33/74* (2013.01); *A61K 38/00* (2013.01); *G01N 2333/58* (2013.01); *G01N 2600/00* (2013.01); *Y10T 428/24802* (2015.01)

(58) Field of Classification Search
CPC .................................................. C08F 220/06
USPC ...................................................... 424/400
See application file for complete search history.

(56) References Cited

U.S. PATENT DOCUMENTS 7,550,441 B2 * 6/2009 Farokhzad et al. .......... A61K 31/7088
514/44
2002/0127623 A1 * 9/2002 Minshull et al. ............ 435/7.92
2013/0011364 A1 * 1/2013 Fichert .................. A61K 31/74
424/78.35

FOREIGN PATENT DOCUMENTS

| | | | |
|---|---|---|---|
| DE | 102009059070 A1 * | 7/2010 | |
| EP | 1 929 299 | 12/2010 | |
| IL | WO 2009083975 A2 * | 7/2009 | ....... G01N 33/54306 |
| WO | WO 2010/081076 | 7/2010 | |
| WO | WO 2010078325 A2 * | 7/2010 | ............. C07K 14/58 |
| WO | WO 2010081076 A2 * | 7/2010 | ........... A61K 9/5138 |

OTHER PUBLICATIONS

Gimzewski et al., Immunological Biosensors, Chapter 15, The Immunoassay Handbook, Third Edition, David Wild editor, 2005, 265-280.*
Sellin, L., European Patent Office, English Machine Translation of DE102009059070, 2010, 1-21.*
Verheyen et al., Challenges for the Effective Molecular Imprinting of Proteins, Biomaterials, 2011, 32, 3008-3020.*
Puoci et al., Molecularly Imprinted Polymers (MIPs) in Biomedical Applications, Biopolymers, 2010, 547-575.*
Opik et al., Molecularly Imprinted Polymers: A New Approach to the Preparatin of Functional Materials, 2009, 58(1), 3-11.*
Yan et al., Characteristic and Synthetic Approach of Molecularly Imprinted Polymer, Int. J. Mol. Sci., 2006, 7, 155-178.*
Bossi A et al., "Molecularly imprinted polymers for the recognition of proteins: The state of the art" *Biosensors and Bioelectronics*, 2007, 22:1131-1137.
Li Y et al., "Selective recognition of veterinary drugs residues by artificial antibodies designed using a computational approach" *Biomaterials*, 2009, 30:3205-3211.
Chen W et al., "Molecularly Imprinted Polymers Having Amidine and Imidazole Functional Groups as an Enzyme-Mimetic Catalyst for Ester Hydrolysis" *Macromolecular Research*, 2002, 10(2):122-126.
Zhang L et al., "Synthesis and characteristics of tyrosine imprinted beads via suspension polymerization" *Reactive & Functional Polymers*, 2003, 56:167-173.
de Bold AJ and Flynn TG, "Cardionatrin I—a novel heart peptide with potent diuretic and natriuretic properties" *Life Sciences*, 1983, 33(3):297-302.
Kangawa K and Matsuo H, "Purification and Complete Amino Acid Sequence of Alpha-Human Atrial Natriuretic Polypeptide (Alpha-hANP)" *Biochemical and Biophysical Research Communications*, 1984, 118:131-139.
Valsson F et al., "Atrial natriuretic peptide attenuates pacing-induced myocardial ischemia during general anesthesia in patients with coronary artery disease" *Anesthesia and Analgesia*, 1999, 88(2):279-285.

(Continued)

*Primary Examiner* — Amy M Bunker
(74) *Attorney, Agent, or Firm* — Saliwanchik, Lloyd & Eisenschenk

(57) ABSTRACT

The present invention concerns molecularly imprinted polymers (MIPs) having an affinity for natriuretic peptides, such as atrial natriuretic peptide (ANP). In some embodiments, the MIP is a nanoparticle (a molecularly imprinted polymeric nanoparticle (MIPNP)). Other aspects of the invention include methods of preparing an MIP having affinity for a natriuretic peptide, methods for binding a natriuretic peptide in vitro or in vivo using an MIP of the invention, methods for interfering with the binding of a natriuretic peptide with its receptor in vivo, methods for reducing inflammation, cell growth, cell differentiation, or a cell proliferation disorder, methods for detecting natriuretic peptides, and devices and kits for sequestering and/or detecting natriuretic peptides.

3 Claims, 16 Drawing Sheets

(56) References Cited

OTHER PUBLICATIONS

Kong X et al., "Natriuretic Peptide Receptor A as a Novel Anticancer Target" *Cancer Research*, 2008, 68(1):249-256.

Herman JP et al., "Localization of natriuretic peptide-activated guanylate cyclase mRNAs in the rat brain" *Journal of Comparative Neurology*, 1996, 369(2):165-187.

Goy MF et al., "Evidence for a novel natriuretic peptide receptor that prefers brain natriuretic peptide over atrial natriuretic peptide" *Biochemical Journal*, 2001, 358:379-387.

Janiak DS and Kofinas P, "Molecular imprinting of peptides and proteins in aqueous media" *Analytical and Bioanalytical Chemistry*, 2007, 389:399-404.

Abbate V et al., "Preparation, Characterization, and Binding Profile of Molecularly Imprinted Hydrogels for the Peptide Hepcidin" *Journal of Polymer Science Part a—Polymer Chemistry*, 2010, 48(8):1721-31.

Hart BR and Shea KJ, "Synthetic Peptide Receptors: Molecularly Imprinted Polymers for the Recognition of Peptides Using Peptide-Metal Interactions" *Journal of the American Chemical Society*, 2001, 123:2072-2073.

Hart BR and Shea KJ, "Molecular imprinting for the recognition of N-terminal histidine peptides in aqueous solution" *Macromolecules*, 2002, 35(16):6192-6201.

Hoshino Y et al., "Peptide Imprinted Polymer Nanoparticles: A Plastic Antibody" *Journal of the American Chemical Society*, 2008, 130:15242-15243.

Rachkov A and Minoura N, "Recognition of oxytocin and oxytocin-related peptides in aqueous media using a molecularly imprinted polymer synthesized by the epitope approach" *Journal of Chromatography A*, 2000, 889(1-2):111-118.

Rachkov A and Minoura N, "Towards molecularly imprinted polymers selective to peptides and proteins. The epitope approach" *Biochimica Et Biophysica Acta-Protein Structure and Molecular Enzymology*, 2001, 1544:255-266.

Hoshino Y et al., "Recognition, Neutralization, and Clearance of Target Peptides in the Bloodstream of Living Mice by Molecularly Imprinted Polymer Nanoparticles: A Plastic Antibody" *Journal of the American Chemical Society*, 2010, 132:6644-6645.

Hoshino Y et al., "Design of Synthetic Polymer Nanoparticles that Capture and Neutralize a Toxic Peptide" *Small*, 2009, 5(13):1562-1568.

Lin CY et al., "Discrimination of Peptides by Using a Molecularly Imprinted Piezoelectric Biosensor" *Chemistry—A European Journal*, 2003, 9:5107-5110.

Flam F, "Molecular imprints make a mark" *Science*, 1994, 263(5151):1221-1222.

Nicholls IA, "Thermodynamic Considerations for the Design of and Ligand Recognition by Molecularly Imprinted Polymers" *Chemistry Letters*, 1995, 24(11):1035-1036.

Nishino H et al., "Selective protein capture by epitope imprinting" *Angewandte Chemie—International Edition*, 2006, 45(15):2392-2396.

Guo W and Hu NF, "Interaction of myoglobin with poly(methacrylic acid) at different pH in their layer-by-layer assembly films: An electrochemical study" *Biophysical Chemistry*, 2007, 129(2-3):163-171.

Li L et al., "Preparation of novel bovine hemoglobin surface-imprinted polystyrene nanoparticles with magnetic susceptibility" *Science in China Series B—Chemistry*, 2009, 52(9):1402-1411.

Potter LR et al., "Natriuretic Peptides, Their Receprots, and Cyclic Guanosin Monophosphate-Dependent Signaling Functions" *Endocrine Reviews*, 2006, 27(1):47-72.

Lee CY et al., "Designer natriuretic peptides" *Journal of Investigative Medicine*, 2009, 57(1):18-21.

Ferris R et al., "Construction and use of two α-human atrial natriuretic peptide-fragment affinity chromatography columns in the isolation of C- and N-terminal epitope-specific antibodies for use in a prototype α-hANP biosensor" *Journal of Chromatography*, 1992, 577(2):251-265.

Zhang W et al., "Plasmid-encoded NP73-102 modulates atrial natriuretic peptide receptor signaling and plays a critical role in inducing terologenic dendritic cells" *Genetic Vaccines and Therapy*, 2011, 9(3):1-12.

Kandasamy R et al., "Isatin down-regulates expression of atrial natiuretic peptide receptor-A and inhibits airway inflammation in a mouse model of allergic asthma" *International Immunopharmacology*, 2010, 10:218-225.

Hoshino Y et al., "The rational design of a synthetic polymer nanoparticle that neutralizes a toxic peptide in vivo" *PNAS*, 2012, 109(1):33-38.

Wang C et al., "Preparation and Characterization of Molecularly Imprinted Polymeric Nanoparticles for Atrial Natriuretic Peptide (ANP)" *Advanced Functional Materials*, 2011, 21:4434-4429.

Li S et al., "Molecularly Imprinted Polymers: Thermodynamic and Kinetic Considerations on the Specific Sorption and Molecular Recognition" *Sensors*, 2008, 8:2854-2864.

\* cited by examiner

Adsorption isotherm curves ($Q_e$ (mg/g) vs. $C_0$) of MIPNP and NIPNPs for template peptide Scatchard plot of MIPNP for template, $Q_e/C_s$ vs. $Q_e$ Adsorption isotherm curves (Qe(mg/g) vs $C_0$) of MIPNP and NIPNPs for ANP Scatchard Curve of MIPNP for ANP ($Q_e/C_s$ vs. $Q_e$)

a  NH$_2$-SLRRSSCFGGRMDRIGAQSGLGCNSFRY-OH

MOLECULARLY IMPRINTED POLYMERS HAVING AFFINITY FOR NATRIURETIC PEPTIDES

CROSS-REFERENCE TO RELATED APPLICATIONS

The present application is the National Stage of International Application Number PCT/US2012/026449, filed Feb. 24, 2012, which claims the benefit of U.S. Provisional Application Ser. No. 61/446,739, filed Feb. 25, 2011, which is hereby incorporated by reference herein in its entirety, including any figures, tables, or drawings.

GOVERNMENT SUPPORT

This invention was made with government support under grant number R01 CA015005 awarded by the National Institutes of Health. The government has certain rights in the invention.

BACKGROUND OF THE INVENTION

Human atrial natriuretic peptide (ANP) is a 28-amino acid polypeptide (human ANP 99-126), which was discovered at the end of 1983 [1] and the beginning of 1984 [2]. ANP is a polypeptide hormone released from the cardiac atria in response to artial stretch and plays an important role in the regulation of body fluid homeostasis [3]. ANP's receptor, natriuretic peptide receptor-A (NPR-A) is expressed on cells in many different tissues of various organ systems and signals through guanylyl cyclase. Both ANP and NPR-A are expressed by lung cancer cells, and oversecretion of ANP has been linked with hyponatremia (14-16). Recently, the inventors' laboratory determined that the expression and signaling of NPR-A is important for tumor growth and could be a new target for cancer therapy [4]. Blocking NPR-A signaling through treatment with nanoparticles conjugated with siNPRA or pNP73-102 attenuated tumorigenesis in lung and ovarian cancers and melanomas by several mechanisms, including decreasing local inflammation, inducing the expression of tumor suppressive gene $R_b$, and blocking vascular endothelial growth factor (VEGF) expression. NPR-A appears to be expressed largely in restricted cell populations containing high levels of ANP. Other studies implicated that the NPR-A receptor is related mainly to the autoregulation of ANP neurons and central control of cardic ANP release [5]. It was also reported that ANP-activated cGMP synthesis provided a good index of NPR-A protein expression, which ranges from maximal in adrenal gland, lung, kidney, and testis to minimal in heart and colon [6]. The disruption of ANP-NPR-A signaling inhibits tumor burden and metastasis.

Molecularly imprinted polymers (MIPs) are synthetic materials produced through cross-linking the functional monomers in the presence of the template molecules. Following removal of the template, the cavities possessing size, shape, and functional group orientation which are complementary to the target molecules are generated [7,8]. The major templates for MIPs have characterized low molecular weight in organic solvents, whereas the aqueous molecular imprinting biomolecules such as peptide and proteins still remains elusive. The main difficulties to imprint the large and flexible proteins include the large molecular dimensions, the flexibility of the chain and low mass-transfer kinetics which limit the polymer molecular recognition capacity and selectivity. A number of different strategies for creating MIP nanoparticles targeting proteins and peptides have been developed. Utilizing functional groups to form strong template interactions such as electrostatic and metal-chelating have been used [9, 10]. For example, MIP nanoparticles synthesis with a functional monomer optimization strategy using hydrophobic and electrostatic function could possess the binding affinity and selectivity for the biological target comparable to those of natural antibodies [11]. The epitope approach using a small sequence of amino acids from the large protein target has been used to create the imprint. The resulting MIP by the epitope approach can successfully bind oxytocin by imprinting Tyr-Pro-Leu-Gly (SEQ ID NO:1) amino acid sequence [12, 13]. Such particles have recently been studied as functional materials for antibodies for capturing and neutralizing toxin peptide [11, 14, 15], protein selective separation and discrimination [16].

BRIEF SUMMARY OF THE INVENTION

The inventors hypothesized that NPR-A expression in cancer cells can be down regulated with ANP concentration in the cell culture media. Moreover, since biological antibodies to NPR-A generally do not provide reproducible results, the inventors further hypothesized that a synthetic neutralizing antibody to ANP which has high selectivity and affinity for ANP can be used to regulate ANP levels and attenuate NPR-A binding to ANP in cancer cells.

An ANP "plastic antibody" (a molecularly imprinted polymer (MIP) nanoparticle) was prepared by an epitope approach using a small sequence of amino acids from the ANP. The hydrodynamic size of the MIP nanoparticles, adsorption kinetics and binding isotherm of MIP nanoparticles for ANP and template were measured. The selectivity of the MIP nanoparticles was also tested.

The present invention concerns molecularly imprinted polymers (MIPs) having an affinity for natriuretic peptides, such as atrial natriuretic peptide (ANP). In some embodiments, the MIP is a nanoparticle (a molecularly imprinted polymeric nanoparticle (MIPNP)). In some embodiments, the MIP has affinity for one or more template regions (also referred to herein as templating regions or epitopes) on the natriuretic peptide, wherein the template region comprises 4, 5, 6, 7, 8, 9, 10, 11, 12, 13, 14, 15, or more contiguous amino acids on the natriuretic peptide.

In some embodiments, the templating region used for the MIP comprises one or more target regions of a natriuretic peptide selected from among atrial natriuretic peptide (ANP; amino acids 99-126 of pro-ANP), long-acting natriuretic peptide (LANP; amino acids 1-30 of pro-ANP), vessel dilator (VD; amino acids 31-67 of pro-ANP), kaliuretic peptide (KP; amino acids 79-98 of pro-ANP), NP73-102 (amino acids 73-102 of pro-ANP), C-type natriuretic peptide (CNP), brain natriuretic peptide (BNP), urodilatin, dendroaspis natriuretic peptide (DNP), or a biologically active fragment of any of the foregoing.

Embodiments of the invention are directed to the preparation of MIPNPs for the recognition and binding of ANP. ANP is a 28-amino acid peptide with a 17-amino acid ring formed by a disulfide bond between two cysterine residues at positions 7 and 23 in the middle of the molecule (shown in FIG. 17A). In some embodiments of the invention, the MIPNPs are formed about a templating region (also referred to herein as an epitope) comprising the N-terminus of the ANP. In some embodiments of the invention, the epitope can be any sequence comprising the amine terminal four through six sequence of ANP as the template. In an embodiment of the invention, the epitope comprises the amine terminal six residue oligopeptide (NH$_2$—SLRRSS—CONH$_2$) (SEQ ID NO:2) as it is outside of the ring formed by the disulfide bonded 17-amino acid ring. The six residues include three positively charged, three polar uncharged (—OH), and one hydrophobic side chain amino acid residues. The MIPNPs can be formed as nanoparticles. The nanoparticles can vary from about 50 to about 2,000 nm in cross-section and can be monodispersed or polydispersed.

The MIPNPs according to embodiments of the invention comprise a vinyl addition polymerized gel having repeating units for cross-linking, repeating units for hydrogen bonding, repeating units for electrostatic interactions, and repeating units for hydrophobic interactions. In one embodiment of the invention, the repeating units of the MIPNPs are those from the copolymerization of methacrylic acid (MAA), N-isopropylacrylamide (NIPAm), and N,N'-methylenebisacrylamide (BIS) for hydrogen bonding and electrostatic interactions, hydrophobic interactions, and cross-linking, respectively. In embodiments of the invention, other monomers can be included or used alternatively to MMA, for example, acrylic acid (AA) can be used for hydrogen bonding and/or electrostatic interaction or acrylamide, methacrylamide, or hydroxyethylacrylate for hydrogen bonding. In embodiments of the invention, other monomers can be included or used alternatively to NIPAm, for example other mono- or bis-alkyl N-substituted acrylamides, such as n-propyl, n-butyl, 2-methylpropyl, t-butyl or higher mono substituted acrylamides, or dimethylacrylamide, methyl ethyl acrylamide, or other acrylamides with at least some water solubility for hydrophobic interactions with the epitope. According to embodiments of the invention, other cross-linking monomers that can be included or used alternatively to BIS include other bis acrylamides, such as piperazine di-acrylamide (PDA), a diacrylate or dimethacrylate terminated ethylene oxide oligomer, diallyltartardiamide (DATD), dihydroxyethylene-bis-acrylamide (DHEBA), and/or bis-acrylylcystamine (BAC). The proportions of the different monomers can vary depending upon the crosslink density and degree of water swelling desired. The molar ratio of crosslinker to hydrogen bonding/electrostatic monomers to hydrophobic monomers can be about 1:2:20 to about 1:5:5. In an embodiment of the invention the MAA to NIPAm to BIS ratio is 1:3:10. The molar ratio of the monomers and the choice of the monomers control the size of the nanoparticles.

In embodiments of the invention, free radical polymerization is employed to prepare MIPNPs at room temperature or other temperature that the MIPNPs are designed to function, for example normal body temperature or elevated body temperature. Polymerization is carried out in a solvent comprising water. In an embodiment of the invention, the solvent can be pure water, a salt solution, or a mixed solvent comprising water, for example a mixture with an alcohol. Polymerization employs a water soluble free radical initiator, for example, ammonium persulfate and N,N,N',N'-tetramethylethylenediamine, a thermal initiator comprising a mixture of a radical source and a free radical promoter. Photoinitiation can be performed where riboflavin or riboflavin phosphate can be included with the ammonium persulfate and N,N,N',N'-tetramethylethylenediamine. The polymerization can be carried out at a pH that is approximately the pH at which the MIPNP is to be used, for example, within one pH unit of the use pH. The pH can be chosen to achieve a desired proportion of deprotonated MMA or other monomer to achieve the electrostatic binding units. The polymerization can be carried out in a stirred or unstirred solution.

BRIEF DESCRIPTION OF SEQUENCES

Figure 1A:
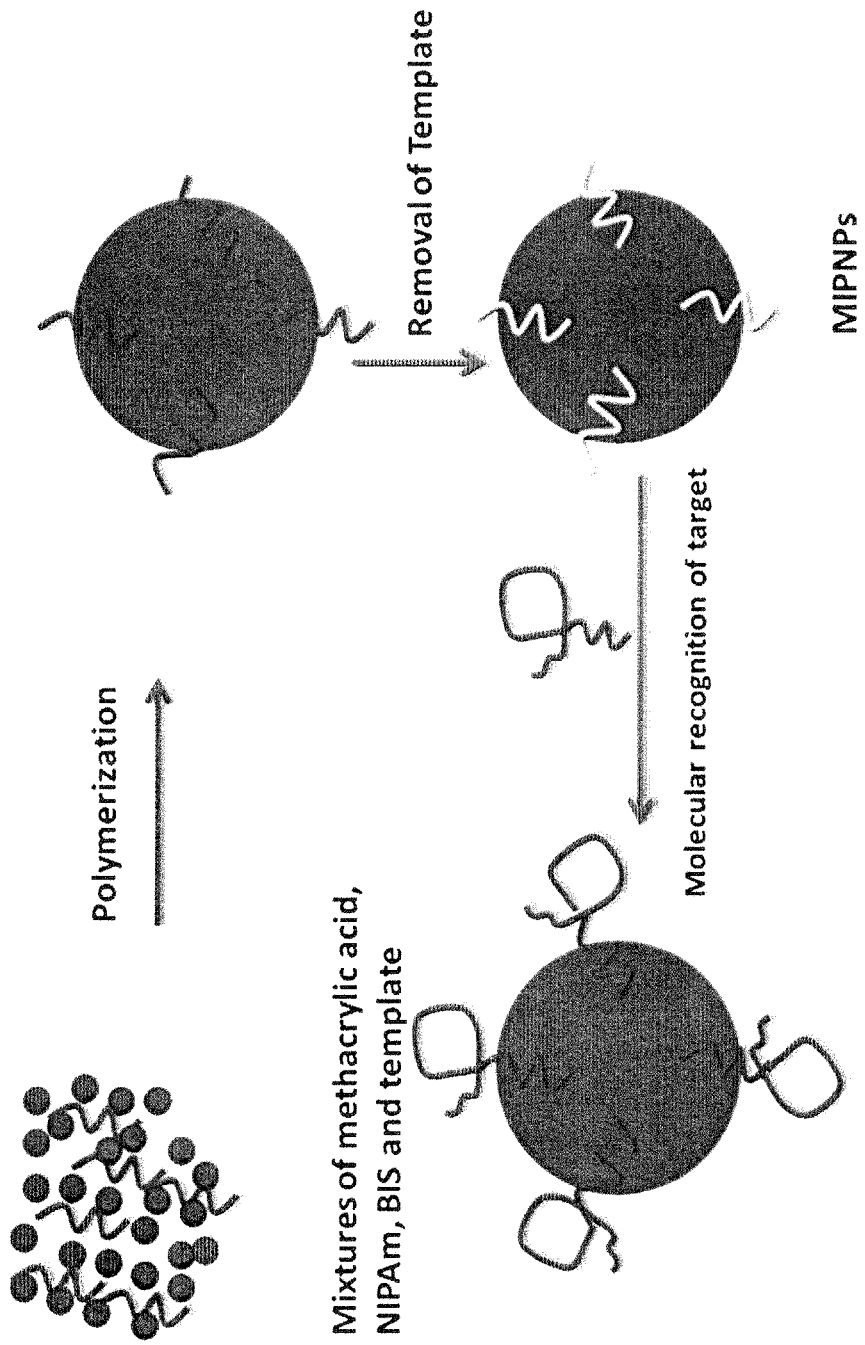
FIGS. 1A and 1B are schematic diagrams depicting preparation of molecularly imprinted polymeric nanoparticles (FIG. 1A) including amino acid structures (FIG. 1B) in accordance with embodiments of the invention.

SEQ ID NO: 1 is a oxytocin-related tetrapeptide useful as an epitope or templating region to produce a molecularly imprinted polymer.

SEQ ID NO:2 is an amine-terminal six-residue oligopeptide of ANP.

SEQ ID NO:3 is the amino acid sequence of human ANP.

SEQ ID NO:4 is the amino acid sequence of human BNP.

SEQ ID NO:5 is the amino acid sequence of human CNP.

SEQ ID NO:6 is the amino acid sequence of human URO.

SEQ ID NO:7 is the amino acid sequence of human LANP.

SEQ ID NO:8 is the amino acid sequence of human VD.

SEQ ID NO:9 is the amino acid sequence of human KP.

SEQ ID NO:10 is the amino acid sequence of human NP73-102.

SEQ ID NO:11 is the amino acid sequence of DNP,

SEQ ID NO:12-SEQ ID NO:14 are conserved amino acid sequences shared by several natriuretic peptides.

DETAILED DISCLOSURE OF THE INVENTION

The natriuretic peptide receptor A (NPR-A), the receptor for cardiac hormone atrial natriuretic peptide (ANP), is expressed abundantly on cancer cells, and disruption of ANP-NPR-A signaling inhibits tumor burden and metastasis. Since biological antibodies to NPR-A do not provide reproducible results, the inventors reasoned that a synthetic neutralizing antibody to ANP which has high selectivity and affinity for ANP can be used to regulate ANP levels and attenuate NPR-A binding to ANP in cancer cells. In this study, the inventors generated a synthetic antibody using molecularly imprinted polymeric nanoparticles (MIPNPs) for ANP and characterized for its binding and affinity. The MIPNP for ANP was prepared by precipitate polymerization using the short peptide (epitope) as template, methacrylic acid and N-isopropylacrylamide as functional monomers, bis-acrylamide as crosslinker. The average diameter of prepared MIPNPs in water was 215.8±4.6 nm and of non-imprinted nanoparticles (NIPNPs) was 197.7±3.1 nm. The binding isotherm analysis indicates that MIPNPs have a much higher binding ability for template molecule and ANP than NIPNPs. Scatchard analysis gave the equilibrium binding constant Ka $1.36 \times 10^5$ mol/l with the binding capacity 10 mol/g for template peptide and the equilibrium binding constant $1.26 \times 10^5$ mol/l with the binding capacity 0.36 mmol/g for ANP peptide. The binding kinetics studies showed that MIPNPs could easily reach the protein adsorption equilibrium in 30 minutes. The results of selectivity demonstrated that MIPNPs had high binding affinity to ANP but lack significant affinity to BSA or scrambled ANP. MIPNPs also demonstrate the selective adsorption of ANP in the cell culture media. The prepared synthetic ANP antibody, MIPNP has higher affinity and selectivity to ANP and may be used for modulating ANP-NPR-A signaling.

The present invention concerns molecularly imprinted polymers (MIPs) having an affinity for natriuretic peptides, such as atrial natriuretic peptide (ANP). In some embodiments, the MIP is a nanoparticle (a molecularly imprinted polymeric nanoparticle (MIPNP)). In some embodiments, the templating region used for the MIP comprises one or more target regions from a naturally occurring natriuretic peptide (e.g., an endogenous natriuretic polypeptide that exists in humans and/or animals), such as ANP, BNP, CNP, urodilatin (URO), LANP, VD, and KP, or the templating region comprises one or more target regions from a natriuretic peptide that is not known to exist in nature, such as NP73-102. In some embodiments, the natriuretic peptide is selected from among:
Human ANP: slrrsscfggrmdrigaqsglgcnsfry (SEQ ID NO:3);
Human BNP: spkmvqgsgcfgrkmdrissssglgckylrrh (SEQ ID NO:4);
Human CNP: ykgankkgls kgcfglkldrigsmsglgc (SEQ ID NO:5);
Human URO: nlghglypdmdpehvgafvdavhk hsrllrqn (SEQ ID NO:6);
Human long acting NP (LANP): npmynavsnadlmdtknlld-hleekmpled (SEQ ID NO:7);
Human Vessel dialator (VD): evvppqvlsepneeagaalsplpcvp-pwtgevspaqr (SEQ ID NO:8);
Human Kaliuretic peptide (KP): ssdrsallksklralltapr (SEQ ID NO:9);
Human NP73-102: grgpwdssdrsallksklralltaprslrr (SEQ ID NO:10); or
Dendroaspis natriuretic peptide (DNP): evkydpcfghkidrin-hvsnlgcpslrdprpnapstsa (SEQ ID NO:11), or a fragment of one of the foregoing peptides.

In some embodiments, the natriuretic peptide used for preparation of the MIP has the amino acid sequence comprising or consisting of CFGXXXDRIXXXXGLGC (SEQ ID NO:12), wherein X is any amino acid (each of which can be the same or different), and wherein the two cysteines are linked (e.g., disulfide-linked) to form a 17-amino acid ring, which is a conserved sequence shared by ANP, BNP, CNP, and urodilatin [22]. In some embodiments, the natriuretic peptide used for preparation of the MIP has the amino acid sequence comprising or consisting of CFGXXXDRIXXXXXLGC (SEQ ID NO: 13), wherein X at positions 4-6 and 10-13 is any amino acid (each of which can be the same or different), wherein X at position 14 is G or N, and wherein the two cysteines are linked (e.g., disulfide-linked) to form a 17-amino acid ring, which is a conserved sequence shared by ANP, BNP, CNP, urodilatin, and DNP [23]. In some embodiments, the templating region is outside of the disulfide bonded 17-amino acid ring. For example, in some embodiments, the templating region is at the N-terminal end or at the C-terminal end of the natriuretic peptide, outside the 17-amino acid ring. In some embodiments, the templating region comprises or consists of the five-amino acid sequence at the N-terminus of ANP (SEQ ID NO:2).

In some embodiments, the templating region is a sequence (e.g., 3, 4, 5, 6, 7, 8, 9, 10, 11, 12, 13, 14, 15 or more contiguous amino acids) of ANP (SLRRSSCFGGRM-DRIGAQSGLGCNSFRY (SEQ ID NO:3) (the bold residues represent amino acids conserved among many natriuretic peptides)) or a sequence (e.g., 3, 4, 5, 6, 7, 8, 9, 10, 11, 12, 13, 14, 15 or more contiguous amino acids) of another peptide having the conserved CFGXXXDRIXXXSGLGC (SEQ ID NO:14) domain, wherein X is any amino acid (each of which can be the same or different) and, optionally, wherein the two cysteines are linked (e.g., disulfide-linked). In some embodiments, the templating region used for the MIP is within or overlaps with this conserved domain. In some embodiments, the templating region used for the MIP is outside of (not within or overlapping with) this conserved domain. In some embodiments, the templating region is at the N-terminus of the natriuretic peptide. In some embodiments, the templating region is at the C-terminus of the natriuretic peptide.

Various polymer imprinting processes may be used to produce MIPs of the invention (see, for example, [28]-[31]).

In some embodiments, the MIP is multi-functional, having an affinity region for a first templating region of a first target natriuretic peptide and having one or more additional affinity regions for different templating regions of the first natriuretic peptide, a different natriuretic peptide, or a different target molecule (e.g., a peptide other than an natriuretic peptide).

The MIPs of the invention can be part of other materials or in an isolated or purified form. The MIPNPs can be formed as nanoparticles. The nanoparticles can vary from about 50 to about 2,000 nm in cross-section and can be monodispersed or polydispersed.

Another aspect of the invention provides a method for binding a natriuretic peptide in vitro or in vivo, comprising contacting an MIP of the invention with the natriuretic peptide. Thus, the MIPs of the invention may be used to bind target natriuretic peptides, separating or purifying them from their milieu (the medium in which they are resident). For example, the MIPs may be attached to a substrate, which is brought in contact with a medium (e.g., a biological sample such as a tissue or body fluid; or a culture supernatant) that contains or potentially contains natriuretic peptides to be bound and, optionally, subsequently separated from the medium. Thus, using the MIPs of the invention, natriuretic peptides may be purified, isolated, or enriched. The MIPs may be used similarly to antibodies as components of a biosensor for detecting and monitoring natriuretic peptides

[24]. The substrate can be, for example, a magnetic particle, a latex particle, a microtiter multi-well plate, a membrane, a bead, a column, a cuvette, or reaction vessel.

Another aspect of the invention provides a method for interfering with the binding of a natriuretic peptide with its receptor (natriuretic peptide receptor) in vivo, comprising contacting an MIP of the invention with the natriuretic peptide.

The MIPs of the invention may be used to treat any condition in a subject in which it is desirable to interfere with the binding of a natriuretic peptide with its receptor and thus inhibit natriuretic peptide receptor signaling, e.g., natriuretic peptide receptor-A (NPR-A) signaling [25][26][27]. Thus, another aspect of the invention concerns a method for reducing inflammation, cell growth, cell differentiation, or a cell proliferation disorder in a human or animal subject, comprising administering an effective amount of an MIP of the invention to the human or animal subject.

Another aspect of the invention provides a pharmaceutical composition comprising an MIP; and a pharmaceutically acceptable carrier. Preferably, the composition contains a sufficient amount of MIP to bind a natriuretic peptide (for example, ANP), in vivo.

Another aspect of the invention concerns a method of preparing an MIP having affinity for a natriuretic peptide, comprising: polymerizing a monomer in the presence of a templating region of a natriuretic peptide; and removing the templating region from the polymerized monomer, thereby forming the MIP.

Another aspect of the invention concerns a method of preparing an MIP having affinity for a natriuretic peptide, comprising:

combining at least one water soluble monomer that provides electrostatic and/or hydrogen bonding functionality, at least one water soluble monomer that provides hydrophobic bonding functionality, and at least one water soluble cross-linking monomer in an aqueous solution;

adding a templating region of a natriuretic peptide;

adding a free radical initiator and, optionally, a radical promoter;

polymerizing the combined monomers and initiators with the precipitation of a polymer gel-templating region complex; and removing the templating region to form a molecularly imprinted polymer having one or more sites for attachment of a natriuretic peptide comprising the templating region.

The MIPNPs according to embodiments of the invention comprise a vinyl addition polymerized gel having repeating units for cross-linking, repeating units for hydrogen bonding, repeating units for electrostatic interactions, and repeating units for hydrophobic interactions. In one embodiment of the invention, the repeating units of the MIPNPs are those from the copolymerization of methacrylic acid (MAA), N-isopropylacrylamide (NIPAm), and N,N'-methylenebisacrylamide (BIS) for hydrogen bonding and electrostatic interactions, hydrophobic interactions, and cross-linking, respectively. In embodiments of the invention, other monomers can be included or used alternatively to MMA, for example, acrylic acid (AA) can be used for hydrogen bonding and/or electrostatic interaction or acrylamide, methacrylamide, or hydroxyethylacrylate for hydrogen bonding. In embodiments of the invention, other monomers can be included or used alternatively to NIPAm, for example other mono- or bis-alkyl N-substituted acrylamides, such as n-propyl, n-butyl, 2-methylpropyl, t-butyl or higher mono substituted acrylamides, or dimethylacrylamide, methyl ethyl acrylamide, or other acrylamides with at least some water solubility for hydrophobic interactions with the epitope. According to embodiments of the invention, other cross-linking monomers that can be included or used alternatively to BIS include other bis acrylamides, such as piperazine di-acrylamide (PDA), a diacrylate or dimethacrylate terminated ethylene oxide oligomer, diallyltartardiamide (DATD), dihydroxyethylene-bis-acrylamide (DHEBA), and/or bis-acrylylcystamine (BAC). The proportions of the different monomers can vary depending upon the crosslink density and degree of water swelling desired. The molar ratio of crosslinker to hydrogen bonding/electrostatic monomers to hydrophobic monomers can be about 1:2:20 to about 1:5:5. In an embodiment of the invention the MAA to NIPAm to BIS ratio is 1:3:10. The molar ratio of the monomers and the choice of the monomers control the size of the nanoparticles.

In embodiments of the invention, free radical polymerization is employed to prepare MIPNPs at room temperature or other temperature that the MIPNPs are designed to function, for example normal body temperature or elevated body temperature. Polymerization is carried out in a solvent comprising water. In an embodiment of the invention, the solvent can be pure water, a salt solution, or a mixed solvent comprising water, for example a mixture with an alcohol. Polymerization employs a water soluble free radical initiator, for example, ammonium persulfate and N,N,N',N'-tetramethylethylenediamine, a thermal initiator comprising a mixture of a radical source and a free radical promoter. Photoinitiation can be performed where riboflavin or riboflavin phosphate can be included with the ammonium persulfate and N,N,N',N'-tetramethylethylenediamine. The polymerization can be carried out at a pH that is approximately the pH at which the MIPNP is to be used, for example, within one pH unit of the use pH. The pH can be chosen to achieve a desired proportion of deprotonated MMA or other monomer to achieve the electrostatic binding units. The polymerization can be carried out in a stirred or unstirred solution.

ANP is a polypeptide hormone released from the cardiac atria in response to artial stretch and plays an important role in the regulation of body fluid homeostasis [3]. ANP's receptor, natriuretic peptide receptor A (NPR-A), is expressed on cells in many different tissues of various organ systems and signals through guanylyl cyclase. Both ANP and NPR-A are expressed by lung cancer cells, and over-secretion of ANP has been linked with hyponatremia (14-16). Recently, it was found out that the expression and signaling of NPR-A is important for tumor growth and could be the new target for cancer therapy [4]. The disruption of ANP-NPR-A signaling inhibits tumor burden and metastasis. The inventors hypothesize that NPR-A expression in cancer cells can be down regulated with ANP concentration in the cell culture media. Since biological antibodies to NPR-A do not provide reproducible results, the inventors reasoned that a synthetic neutralizing antibody to ANP which has high selectivity and affinity for ANP can be used to regulate ANP levels and attenuate NPR-A binding to ANP in cancer cells. Molecularly imprinted polymers (MIPs) are synthetic materials produced through cross-linking the functional monomers in the presence of the template molecules. Following removal of the template, the cavities possessing size, shape, and functional group orientation, which are complementary to the target molecules that are generated [7, 8]. The main difficulties to imprint the large and flexible proteins include the large molecular dimensions, the flexibility of the chain and low mass-transfer kinetics which limit the polymer molecular recognition capacity and selectivity. The epitope approach, using a small sequence of amino acids from the large polypeptide target, has been used to create the imprint. The resulting MIP by the epitope approach can successfully bind oxytocin by imprinting Tyr-Pro-Leu-Gly (SEQ ID NO:1) amino acid sequence [12, 13]. Such particles have recently been studied as functional materials for antibodies for capturing and neutralizing toxin peptide [11, 14, 15], protein selective separation and discrimination [16].

Herein, ANP plastic antibody, molecularly imprinted nanoparticle, was prepared by the epitope approach using a small sequence of amino acids from the ANP. The hydrodynamic size of the MIP nanoparticles, adsorption kinetics and binding isotherm of MIP nanoparticles for ANP and template were measured. The selectivity of the MIP nanoparticles was also tested.

The natriuretic peptide receptor-A (NPR-A), the receptor for cardiac hormone atrial natriuretic peptide (ANP), is expressed abundantly on cancer cells, and disruption of ANP-NPR-A signaling inhibits tumor burden and metastasis. Since biological antibodies to NPR-A do not provide reproducible results, the inventors reasoned that a synthetic neutralizing antibody to ANP which has high selectivity and affinity for ANP can be used to regulate ANP levels and attenuate NPR-A binding to ANP in cancer cells. In this study, the inventors generated a synthetic antibody using molecularly imprinted polymeric nanoparticles (MIPNPs) for ANP and characterized its binding and affinity.

The MIPNP for ANP was prepared by precipitate polymerization using the short peptide (epitope) as template, methacrylic acid and N-isopropylacrylamide as functional monomers, bis-acrylamide as crosslinker. The average diameter of prepared MIPNPs in water was 215.8±4.6 nm and of non-imprinted nanoparticles (NIPNPs) was 197.7±3.1 nm. The binding isotherm analysis indicates that MIPNPs have a much higher binding ability for template molecule and ANP than NIPNPs. Scatchard analysis gave the equilibrium binding constant Ka $1.36\times10^5$ mol/l with the binding capacity 10 µmol/g for template peptide and the equilibrium binding constant $1.26\times10^5$ mol/l with the binding capacity 0.36 mmol/g for ANP peptide. The binding kinetics studies showed that MIPNPs could easily reach the protein adsorption equilibrium in 30 min. The results of selectivity demonstrated that MIPNPs had high binding affinity to ANP but lack significant affinity to BSA or scramble ANP. MIPNPs also demonstrate the selective adsorption of ANP in the cell culture media. The prepared synthetic ANP antibody, MIPNP has higher affinity and selectivity to ANP and may be used for modulating ANP-NPR-A signaling.

The plastic antibody ANP (MIPNP) was prepared by precipitate polymerization using epitope approach. The average diameter of prepared MIPNPs in water was 215.8±4.6 nm which is a little bit higher than NIPNPs 197.7±3.1 nm. According to the binding isotherm results, this MIPNP exhibited a much higher binding ability for template molecule and ANP than NIPNPs. Scatchard analysis gave the equilibrium binding constant Ka$1.36\times10^5$ M$^{-1}$ with maximum binding capacity 86 mol/g polymer for template peptide and binding constant $1.26\times10^5$ M$^{-1}$ with maximum binding capacity 0.4 mmol/g for target ANP peptide. The binding kinetics studies showed that MIPNPs could easily reach the protein adsorption equilibrium. The results of selectivity demonstrated that MIPNIPs had high affinity to ANP but lack affinity to BSA or scrambled ANP. The prepared synthetic ANP antibody, MIPNP has higher affinity and selectivity to ANP and will be further studied for modulating ANP-NPR-A signaling.

In another aspect, the present invention concerns pharmaceutical compositions containing an MIP of the invention, and a pharmaceutically acceptable carrier. The pharmaceutical composition can be adapted for the route of administration to the patient, such as to the airways, e.g., nose, sinus, throat and lung, for example, as nose drops, as nasal drops, by nebulization as an inhalant, vaporization, or other methods known in the art. Administration can be continuous or at distinct intervals as can be determined by a person skilled in the art.

The pharmaceutical compositions of the subject invention can be formulated according to known methods for preparing pharmaceutically useful compositions. Furthermore, as used herein, the phrase "pharmaceutically acceptable carrier" means any of the standard pharmaceutically acceptable carriers. The pharmaceutically acceptable carrier can include diluents, adjuvants, and vehicles, as well as implant carriers, and inert, non-toxic solid or liquid fillers, diluents, or encapsulating material that does not react with the active ingredients of the invention. Examples include, but are not limited to, phosphate buffered saline, physiological saline, water, and emulsions, such as oil/water emulsions. The carrier can be a solvent or dispersing medium containing, for example, ethanol, polyol (for example, glycerol, propylene glycol, liquid polyethylene glycol, and the like), suitable mixtures thereof, and vegetable oils. Formulations containing pharmaceutically acceptable carriers are described in a number of sources which are well known and readily available to those skilled in the art. For example, *Remington's Pharmaceutical Sciences* (Martin E W [1995] Easton Pa., Mack Publishing Company, 19$^{th}$ ed.) describes formulations that can be used in connection with the subject invention. Formulations suitable for parenteral administration include, for example, aqueous sterile injection solutions, which may contain antioxidants, buffers, bacteriostats, and solutes which render the formulation isotonic with the blood of the intended recipient; and aqueous and nonaqueous sterile suspensions which may include suspending agents and thickening agents. The formulations may be presented in unit-dose or multi-dose containers, for example sealed ampoules and vials, and may be stored in a freeze dried (lyophilized) condition requiring only the condition of the sterile liquid carrier, for example, water for injections, prior to use. Extemporaneous injection solutions and suspensions may be prepared from sterile powder, granules, tablets, etc. It should be understood that in addition to the ingredients particularly mentioned above, the formulations of the subject invention can include other agents conventional in the art having regard to the type of formulation in question.

The MIPs can be administered to a subject by any desirable route that can achieve the desired outcome (e.g., treatment of cancer or a respiratory disorder). For treatment, the MIKPs can be administered by any route that results in prevention (e.g., delay of onset) or alleviation of one or more symptoms associated with a disorder. For example, the MIP can be administered parenterally, intravenously (I.V.), intramuscularly (I.M.), subcutaneously (S.C.), intradermally (I.D.), orally, intranasally, etc. Examples of intranasal administration can be by means of a spray, drops, powder or gel and also described in U.S. Pat. No. 6,489,306, which is incorporated herein by reference in its entirety. Some embodiments of the present invention involve the administration of the MIP as a nasal spray. Alternate embodiments include administration through any oral or mucosal routes, sublingual administration and even eye drops. However, other means of drug administrations are well within the scope of the present invention.

The MIPs are administered to patients and dosed in accordance with good medical practice, taking into account the clinical condition of the individual patient, the site and method of administration, scheduling of administration, patient age, sex, body weight, and other factors known to medical practitioners. Preferably, an effective amount of MIP is administered to achieve the desired result. The pharmaceutically "effective amount" for purposes herein is thus determined by such considerations as are known in the art. For example, an effect amount of MIP is that amount necessary to bind the target natriuretic peptide. For treatment, the amount of MIP should be effective to achieve improvement including but not limited to total prevention and to improved survival rate or more rapid recovery, or improvement or elimination of signs or symptoms associated with disorders and other indicators as are selected as appropriate measures by those skilled in the art. In accordance with the present invention, a suitable single dose size is a dose that is capable of preventing (delaying or avoiding onset) or alleviating (reducing or eliminating) a sign or symptom in a patient when administered one or more times over a suitable time period. One of skill in the art can readily determine appropriate single dose sizes for systemic administration based on the size of a mammal and the route of administration.

MIPs of the invention may be used to screen for compounds or methods that affect natriuretic peptide activity, natriuretic peptide receptor (e.g., NPR-A) activity, and/or interaction between the peptide having the templating region and the peptide's receptor. The molecular imprinting approach is a technique that is based on the preparation of polymeric sorbents that are selectivity predetermined for a particular substance, or group of structural analogs. Functional and, optionally, cross-linking monomers are allowed to interact with a template molecule (referred to herein as having a templating region or epitope), i.e., a peptide. Polymerization is induced and during this process, the peptide of interest is entrapped within the polymer. After stopping the polymerization, the template molecule is washed out. The resultant imprint of the one or more templating regions of the template molecule is maintained in the rigid polymer and possesses a steric (size, shape) and chemical (special arrangement of complementary functionality) memory for the template. Preferably, the MIP can bind the template (analyte) with specificity similar or superior to that of the antigen-antibody interaction.

In addition to applications in solid-phase extraction and chromatography, MIPs of the invention may be employed in immunoassays or used as an analyte binder in conjunction with a sensor element. A synthetic antibody to natriuretic peptides such as ANP does not such exist. The MIPs of the invention may be employed as a synthetic antibody useful in sequestering natriuretic peptides such as ANP in vitro such as in cell culture and in biological samples such as blood, and may also be used to in vivo modulate inflammation, cell growth, cell differentiation and other disorders in which the pathogenesis involves template natriuretic peptides (e.g., such as disorders involving the interaction between a template natriuretic peptide and its receptor, such as NPR-A). For example, the MIPs may be used in vitro to separate or detect and, optionally, quantify, peptides having the template region in a sample (e.g., a biological sample such as whole blood, plasma, or serum), by contacting the MIP with the sample and detecting the amount of peptides having the template region that have bound to the MIP.

The MIPs may be used similarly to antibodies as components of a biosensor for detecting and monitoring natriuretic peptides [24]. Thus, another aspect of the invention concerns a method for detecting natriuretic peptides, comprising contacting an amount of MIP of the invention with a medium that potentially contains natiuretic peptides for which the MIP has affinity, under conditions that allow binding of the MIP to the natriuretic peptides; and detecting the MIP bound to natriuretic peptides. The detecting step may be qualitative, semi-quantitative, or quantitative, in which the amount of MIP bound to natriuretic peptides is determined. The contacting step may be carried out in vitro or in vivo. The natriuretic peptide detection method of the invention may be used to detect natriuretic peptides (such as ANP), in a medium such as a body fluid or tissue from a human or animal subject. Thus, the detection method may be used to determine the presence and/or levels of specific natriuretic peptides or groups (classes) of natriuretic peptides that are useful as biomarkers (representing the status of the subject or a disease condition). In some embodiments, the medium is a sample of whole blood, blood serum, or blood plasma from a human or animal subject. The MIP may be associated with a detectable moiety (a label), with the detecting step involving detecting the detectable moiety. In some embodiments, the amount of detectable moiety is detected (quantitatively), and the amount of detectable moiety is representative of the amount of natriuretic peptides bound to the MIP. For example, after separation of the resulting labeled natriuretic peptide that has become bound to the MIP (bound fraction) from that volume of medium and/or natriuretic peptides which has remained unbound (unbound fraction), the amount of the detectable moiety (label) in either bound or unbound fraction can be measured and may be correlated with the amount of natriuretic peptide in the sample in any conventional manner, e.g., by comparison to a standard curve. In some embodiments, the method includes comparing the detected amount of MIP bound to natriuretic peptides in the medium to a reference amount (reference level), such as the amount of the natriuretic peptide normally associated with a healthy subject, or to a prior natriuretic peptide level determined for the same subject, or a natriuretic peptide level that is associated with a disease condition or status of health. Thus, in some embodiments, the reference amount correlates with a disease state. In some embodiments, the reference amount correlates with lack of a disease state (normalcy or health). For example, the reference amount to which the test amount is compared may be a threshold or cutoff. Optionally, the MIP may be attached to a substrate when the MIP is contacted with the medium that potentially contains the natriuretic peptide(s) to which the MIP has affinity. The substrate can be, for example, a magnetic particle, a latex particle, a microtiter multi-well plate, a bead, a column, a membrane, a cuvette, or reaction vessel. The templating region(s) may be selected such that the resulting MIP is selective (having affinity) for a specific peptide (i.e., only the specific natriuretic peptide has the selected templating region, e.g., ANP) or the templating region(s) may be selected such that the resulting MIP has affinity for more than one natriuretic peptide (e.g., ANP and CNP).

Another aspect of the invention concerns a device for sequestering or detecting natriuretic peptides, comprising a substrate with one or more MIPs of the invention attached thereto. The device may be contacted with a medium in vitro or in vivo that potentially contains the target natriuretic peptide(s), using a method of the invention. Optionally, the MIP further comprises a detectable moiety (label) that produces signal indicating that the target analyte (natriuretic peptide) is bound thereto. The substrate can be, for example, a magnetic particle, a latex particle, a microtiter multi-well plate, a bead, a membrane, a cuvette, or reaction vessel.

In those embodiments of the methods, devices, and kits of the invention in which a detectable moiety (label) is used, the moiety can be an enzyme or a chemiluminescent moiety, for example, or a radioactive isotope, a fluorophore, a detectable ligand (e.g., detectable by a secondary binding by a labeled binding partner for the ligand), and the like. For in vivo applications, any detectable moiety that is pharmaceutically acceptable (non-toxic at the desired amounts and compatible with the physiology of the subject). In some embodiments, the label is a radionuclide. In some embodiments, the label is iodine-129, iodine-131, or chromium-51. In some embodiments, the detectable moiety is a fluorescent dye.

As indicated above, the methods of the invention can be carried out on a solid support (e.g., using a device of the invention). The solid supports used may be those which are conventional for the purpose of assaying an analyte in a biological sample, and are typically constructed of materials such as cellulose, polysaccharide such as Sephadex, and the like, and may be partially surrounded by a housing for protection and/or handling of the solid support. The solid support can be rigid, semi-rigid, flexible, elastic (having shape-memory), etc., depending upon the desired application. Natriuretic peptides can be detected in a sample in vivo or in vitro (ex vivo). When, according to an embodiment of the invention, the amount of natriuretic peptide in a sample is to be determined without removing the sample from the body (i.e., in vivo, such as with an indwelling catheter or probe), the support should be one which is harmless to the subject and may be in any form convenient for insertion into an appropriate part of the body. For example, the support may be a probe made of polytetrafluoroethylene, polystyrene or other rigid non-harmful plastic material and having a size and shape to enable it to be introduced into a subject. The selection of an appropriate inert support is within the competence of those skilled in the art, as are its dimensions for the intended purpose.

A contacting step in an assay (method) of the invention can involve contacting, combining, or mixing the biological sample and the solid support, such as a reaction vessel, microvessel, tube, microtube, well, multi-well plate, membrane, or other solid support. In an embodiment of the invention, the solid support to be contacted with the biological sample (e.g., blood) has an absorbent pad or membrane for lateral flow of the liquid medium to be assayed, such as those available from Millipore Corp. (Bedford, Mass.), including but not limited to Hi-Flow Plus™ membranes and membrane cards, and SureWick™ pad materials.

The diagnostic device useful in carrying out the methods of the invention can be constructed in any form adapted for the intended use. Thus, in one embodiment, the device of the invention can be constructed as a disposable or reusable test strip or stick to be contacted with a blood sample or blood derived sample for which the presence of the natriuretic peptide or natriuretic peptide level is to be determined. In another embodiment, the device can be constructed using art recognized micro-scale manufacturing techniques to produce needle-like embodiments capable of being implanted or injected into an anatomical site, such as a vein or artery, for indwelling diagnostic applications. In other embodiments, devices intended for repeated laboratory use can be constructed in the form of an elongated probe or catheter, for sampling of blood.

The subject invention also concerns kits for the sequestration and/or detection of one or more natriuretic peptides. In one embodiment, a kit of the invention comprises, in one or more separate containers, one or more MIPs of the invention. Optionally, the one or more MIPs are attached to a substrate. The kits may include one or more devices of the invention. Kits of the invention can also optionally comprise additional reagents. Kits of the invention can also optionally contain packaging information and/or instructions for use of the kit reagents in a method of the invention. Containers in a kit of the invention can be composed of any suitable material, such as glass or plastic.

It has been demonstrated that, in contrast to prior knowledge that ANP decreases inflammatory mechanisms in macrophages, ANP actually increases lung inflammation and this is caused by ANP-NPR-A signaling. This signaling can be blocked by utilizing a small interference RNA (siRNA) approach, in which specific siRNAs targeted to NPR-A can significantly decrease the inflammation. This results in amelioration of inflammation in allergic disease which may be caused by allergens and exacerbated by respiratory viral infections, pollutants, and smoke. Also, this may be beneficial in the amelioration of inflammation and tumorigenesis in cancers. Accordingly, MIPs of the invention may be used to treat or to prevent (e.g., delay or eliminate onset of) inflammatory disorders (e.g., asthma and allergic diseases) and cell proliferation disorders (e.g., cancer) in humans and animals, including but not limited to those disorders disclosed in U.S. Patent Publication No. 2005/0272650 (Mohapatra S., published Dec. 8, 2005), U.S. Patent Publication No. 2007/0265204 (Mohapatra S et al., published Nov. 15, 2007), and U.S. Patent Publication No. 2008/0214437 (Mohapatra S. et al., published Sep. 4, 2008), each of which is incorporated herein by reference in its entirety.

Mammalian species which benefit from the MIPs and methods of the invention include, and are not limited to, apes, chimpanzees, orangutans, humans, monkeys; domesticated animals (e.g., pets) such as dogs, cats, guinea pigs, hamsters, Vietnamese pot-bellied pigs, rabbits, and ferrets; domesticated farm animals such as cows, buffalo, bison, horses, donkey, swine, sheep, and goats; exotic animals typically found in zoos, such as bear, lions, tigers, panthers, elephants, hippopotamus, rhinoceros, giraffes, antelopes, sloth, gazelles, zebras, wildebeests, prairie dogs, koala bears, kangaroo, opossums, raccoons, pandas, hyena, seals, sea lions, elephant seals, otters, porpoises, dolphins, and whales. Non-mammalian animals may also benefit. The terms "patient", "subject", and "individual" are used interchangeably and intended to include such human and non-human animal species. According to the in vivo methods of the present invention, human or non-human natriuretic peptides may be used as the template molecule for the MIPs to be administered to the patient. The template natriuretic peptide may be naturally occurring within the patient and/or the patient's species or a different animal species, or a homolog or fragment thereof. In some embodiments, the template natriuretic peptide used for the MIP is one normally found in the patient to which the MIP is to be administered. In some embodiments, the template natriuretic peptide is one not normally found in the patient or one which is elevated before, during or after a disease state.

As used herein, the terms "peptide", "polypeptide", and "protein" are used interchangeably to refer to a chain of amino acids (a sequence) of any length unless otherwise specified.

As used herein, the term "co-administration" and variations thereof refers to the administration of two or more agents simultaneously (in one or more preparations), or consecutively. For example, one or more types of polypeptides or polypeptide-encoding nucleic acid molecules of the invention can be co-administered with other agents. The MIPs of the invention may be co-administered with one or more other agents.

As used herein, the terms "administer", "apply", "treat", "deliver", and grammatical variations thereof, are used interchangeably to provide MIPs of the subject invention to contact and bind target regions of natriuretic peptides in vitro or in vivo.

In some embodiments, the natriuretic peptide is a homolog. As used herein, the term "homolog" includes allelic variants, splice variants, natural mutants, induced mutants, mammalian orthologs, and other variants that have sufficient amino acid homology (e.g., percentage identity) to a reference natriuretic polypeptide to retain biological activity or to have a shared characteristic of natriuretic polypeptides, which can be measured in an appropriate in vitro or in vivo assay.

As used herein, the term "biologically active" and "biological activity" in the context of natriuretic polypeptides, and homologs and fragments of natriuretic polypeptides, refers to a one or more characteristics of a natriuretic polypeptide such as capability to suppress mean arterial pressure, increase diuresis, increase natriuresis (e.g., by inhibition of renal $Na^+$—$K^+$-ATPase and enhancement of prostaglandin $E_2$ synthesis, or through cGMP), induce vasorelaxation, suppress aldosterone, inhibit DNA synthesis in cancer cells, and decrease expression of vascular endothelial growth factor (VEGF). In some embodiments, the polypeptide of the invention exhibits at least one activity selected from among natriuretic, renin-suppressing, diuretic, and vasodilator activity.

As used in this specification, including the appended claims, the singular "a", "an", and "the" are inclusive of the plural reference unless the context dictates otherwise. Thus, for example, a reference to "a peptide" includes one or more such peptides. A reference to "a target region" is inclusive of more than one such target region. A reference to "a MIP" includes more than one such MIP, and so forth.

The terms "comprising", "consisting of" and "consisting essentially of" are defined according to their standard meaning. The terms may be substituted for one another throughout the instant application in order to attach the specific meaning associated with each term.

The following are exemplified embodiments:

Embodiment 1

A molecularly imprinted polymer (MIP) having affinity for a natriuretic peptide or a fragment thereof.

Embodiment 2

The MIP of embodiment 1, wherein the MIP is a nanoparticle.

Embodiment 3

The MIP of embodiment 1 or 2, wherein the natriuretic peptide is selected from among atrial natriuretic peptide (ANP; amino acids 99-126 of pro-ANP), long-acting natriuretic peptide (LANP; amino acids 1-30 of pro-ANP), vessel dilator (VD; amino acids 31-67 of pro-ANP), kaliuretic peptide (KP; amino acids 79-98 of pro-ANP), NP73-102 (amino acids 73-102 of pro-ANP), C-type natriuretic peptide (CNP), brain natriuretic peptide (BNP), urodilatin, dendroaspis natriuretic peptide (DNP), or a biologically active fragment of any of the foregoing.

Embodiment 4

The MIP of embodiment 1 or 2, wherein the natriuretic peptide is atrial natriuretic peptide (ANP).

Embodiment 5

The MIP of any one of embodiments 1 to 4, wherein the natriuretic peptide comprises SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, or SEQ ID NO:14.

Embodiment 6

The MIP of any one of embodiments 1 to 5, wherein the natriuretic peptide consists of SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, or SEQ ID NO:14.

Embodiment 7

The MIP of any one of embodiments 1 to 6, wherein the MIP has affinity for an N-terminal region of the natriuretic peptide or fragment thereof.

Embodiment 8

A method for binding a natriuretic peptide in vitro or in vivo, comprising contacting a molecularly imprinted polymer (MIP) of any one of embodiments 1 to 7 with the natriuretic peptide.

Embodiment 9

A method for interfering with the binding of a natriuretic peptide with its receptor (natriuretic peptide receptor) in vivo, comprising contacting a molecularly imprinted polymer (MIP) of any one of embodiments 1 to 7 with the natriuretic peptide.

Embodiment 10

A method for reducing inflammation, cell growth, cell differentiation, or a cell proliferation disorder in a human or animal subject, comprising administering an effective amount of a molecularly imprinted polymer (MIP) of any one of embodiments 1 to 7 to the human or animal subject.

Embodiment 11

A pharmaceutical composition comprising a molecularly imprinted polymer (MIP) of any one of embodiments 1 to 7; and a pharmaceutically acceptable carrier.

Embodiment 12

A method of preparing a molecularly imprinted polymer (MIP) having affinity for a natriuretic peptide, comprising: polymerizing a monomer in the presence of a templating region of a natriuretic peptide; and removing the templating region from the polymerized monomer, thereby forming the MIP.

Embodiment 13

The method of embodiment 12, wherein the MIP is an MIP of one of embodiments 2 to 7.

Embodiment 14

A method of preparing a molecularly imprinted polymer (MIP) having affinity for a natriuretic peptide, comprising:
combining at least one water soluble monomer that provides electrostatic and/or hydrogen bonding functionality, at least one water soluble monomer that provides hydrophobic bonding functionality, and at least one water soluble cross-linking monomer in an aqueous solution;
adding a templating region of a natriuretic peptide;
adding a free radical initiator and, optionally, a radical promoter;
polymerizing the combined monomers and initiators with the precipitation of a polymer gel-templating region complex; and
removing the templating region to form a molecularly imprinted polymer having one or more sites for attachment of a natriuretic peptide comprising the templating region.

Embodiment 15

The method of embodiment 14, wherein the templating region is an N-terminal oligomer of the natriuretic peptide.

Embodiment 16

The method of embodiment 14 or 15, wherein the natriuretic peptide is atrial natriuretic peptide (ANP).

Embodiment 17

The method of embodiment 14, wherein the monomers comprise methacrylic acid (MAA), N-isopropylacrylamide (NIPAm), and N,N'-methylenebisacrylamide (BIS).

Embodiment 18

The method of embodiment 17, wherein the MAA:NIPAm:BIS molar ratio is 1:3:10.

Embodiment 19

The method of embodiment 14, wherein the MIP is an MIP of one of embodiments 2 to 7.

Embodiment 20

A method for detecting natriuretic peptides, comprising contacting an amount of MIP of any one of embodiments 1 to 7 with a medium that potentially contains natiuretic peptides for which the MIP has affinity, under conditions that allow binding of the MIP to the natriuretic peptides; and detecting the MIP bound to natriuretic peptides.

Embodiment 21

The method of embodiment 20, wherein said detecting comprises detecting the amount of MIP bound to natriuretic peptides.

Embodiment 22

The method of embodiment 20 or 21, wherein said contacting occurs in vivo.

Embodiment 23

The method of embodiment 20 or 21, wherein said contacting occurs in vitro.

Embodiment 24

The method of any one of embodiments 20 to 23, wherein the medium is a body fluid or tissue.

Embodiment 25

The method of embodiment 24, wherein said contacting occurs in vitro, and wherein the medium is a sample of whole blood, blood serum, or blood plasma from a human or animal subject.

Embodiment 26

The method of any one of embodiments 20 to 25, wherein the MIP is associated with a detectable moiety, and wherein said detecting comprises detecting the detectable moiety.

Embodiment 27

The method of embodiment 26, wherein the amount of detectable moiety is detected (quantitatively), and wherein the amount of detectable moiety is representative of the amount of natriuretic peptides bound to the MIP.

Embodiment 28

The method of any one of embodiments 20 to 27, further comprising comparing the detected amount of MIP bound to natriuretic peptides in the medium to a reference amount (e.g., a control or standard).

Embodiment 29

The method of embodiment 28, wherein the reference amount correlates with a disease state or lack of a disease state.

Embodiment 30

A device for sequestering or detecting natriuretic peptides, comprising a substrate with one or more MIPs of any one of embodiments 1 to 7 attached thereto.

Embodiment 31

The device of embodiment 30, wherein the substrate is a particle, bead, membrane, column, or multi-well plate.

Embodiment 32

The device of embodiment 30 or 31, wherein the one or more MIPs further comprise a detectable moiety associated with the MIP.

Embodiment 33

A kit for sequestration and/or detection of one or more natriuretic peptides, comprising, in one or more separate containers, one or more molecularly imprinted polymers (MIPs) of any one of embodiments 1 to 7.

Embodiment 34

The kit of embodiment 33, further comprising a substrate, wherein the one or more MIPs are attached to the substrate.

All patents, patent applications, provisional applications, and publications referred to or cited herein, supra or infra, are incorporated by reference in their entirety, including all figures and tables, to the extent they are not inconsistent with the explicit teachings of this specification.

Following are examples which illustrate procedures for practicing the invention. These examples should not be construed as limiting. All percentages are by weight and all solvent mixture proportions are by volume unless otherwise noted.

Materials and Methods

Materials.

Methacrylic acid (MAA), ethyl alcohol and N-isopropylacrylamide (NIPAM) were obtained from Across Organics. Ammonium persulfate (APS), sodium bicarbonate and Bis-acrylamide (BS) were purchased from Fisher Scientific. Lauryl sulfate (SDS), 2-mercaptoethanol and Albumin from bovine serum were purchased from Sigma Aldrich. N,N,N',N'-Tetramethylethylenediamie (TMED) was obtained from Fisher Bioreagent. Atrial natriuretic peptide (ANP) was obtained from Ana Spec Inc., Mouse scramble ANP peptide and template peptide were purchased from Biosynthesis.

Synthesis of Molecularly Imprinted Polymer Nanoparticles.

To prepare molecularly imprinted polymer nanoparticles, first 10 mmol (0.1582 g) BIS was dissolved in 50 mL SDS (10 mg) aqueous solution in a 250 mL two-neck round bottom flask. After 1 mmol (0.11 g) NIPAM, 3 mmol (30 μl) MAA and 1.5 g APS were dissolved in the BIS solution, the template peptide (0.7 mg, 1 μmol) was added to the solution. After purging the solution with argon gas for 5 min, TEMD (40 μl) was added. The solution was protected with argon gas at room temperature under stirring at 1000 rpm. After 15 min, the white precipitated was shown in the flask. After 24 hours reaction, the suspension was centrifuged at 3000 rpm for 15 min. After removal of the supernatant, the white product was washed with 10 wt % acetic acid until no peptide can be determined. The prepared MIP nanoparticles were freeze-dried for further use. The non-imprinted polymer nanoparticles (NIPNPs) were prepared under identical conditions as MIPNPs in the absence of template.

Size Measurement.

The hydrodynamic diameters of the purified MIPNPs and NIPNP were determined by a DynaPro DLS Plate reader (Wyatt Technology). The MIPNP and NIPNP were dispersed in deionized water by sonicating 1 min using Sonic Dismembrator (Fisher Scientific) at 5 watts. A minimum of three measurements were taken and averaged for each sample.

Measurement of Template Peptide, ANP, BSA and Scramble ANP.

The measurement of template peptide, ANP, BSA and scramble ANP was using fluoraldehyde (OPA) reagent solution. OPA reagent was prepared by dissolving 5 mg of OPA, 100 μl of pure Ethanol, and 5 μl of b-2-mercaptoethanol in 10 ml of 50 mM carbonate buffer pH 10.5. This OPA reagent was protected from direct light, and used within 2 hours. A set of the protein/peptide standards of known concentration was prepared by dissolving the standard protein/peptide in the same condition as the unknown sample. First, about 10 μl of various sample was added in opaque 96-well plate, then 100 μl of OPA reagent was added and mixed well with the samples. The de-ionized water and MIPNP or NIPNP nanoparticles after centrifugation were used as blanks respectively of standard, MIPNP and NIPNP samples. After 5 min, the fluorescence was measured at excitation 330-390 nm and emission at 436-475 nm. The blank's fluorescence was subtracted from the fluorescence emission values of the sample and standards to determine net fluorescence. The net relative fluorescence of the standards versus concentration was plotted. The concentration of the unknown was calculating using the standard curve.

Binding Experiments.

Binding isotherm experiments of MIPNPs and NIPNPs were carried out using batchwise adsorption method. The bulk template peptide or ANP solutions (1 mg/ml) were prepared by dissolving the peptide in deionized water. MIPNPs or NIPNPs were suspended in autoclaved PBS solution in 0.05 mg/ml and ultrasonicated for 5 sec with 5 watts. Different amount of bulk peptide solution was added to MIPNP or NIPNPs suspension. The suspensions were oscillated in a shaking incubator at 4° C. for 30 min to reach adsorption equilibrium. After adsorption, the peptide concentration in the supernatant after centrifugation was determined. Equilibrium adsorption capacity $Q_e$ (μg/mg) was calculated by mass balance according to the following equation:

$$Q_e = (C_0 - C_S)V/m \tag{1}$$

Where m is the mass (mg) of MIPNP, V (ml) is the volume of protein solution, and $C_0$ (μg/ml) and $C_e$ (μg/ml) are the peptide concentrations of initial solution and the supernatant at equilibrium, respectively.

In dynamic adsorption experiments, the MIPNP and template or ANP peptide suspensions in the 1.5 ml centrifuge tubes were shaken at 4° C. The tubes were taken out at certain intervals and the template concentration in the supernatant was measured. The absorbance $Q_t$ (μg/mg), i.e. dynamic adsorption capacity at time t, was calculated according to the following equation:

$$Q_t = (C_0 - C_t)V/m \tag{2}$$

Where $C_t$ (μg/ml) is the template concentration in the supernatant at time t.

Selectivity Test of MIPNP.

Selectivity tests were carried out by adding 32 μl of BSA, scramble ANP or ANP to 100 μl of 0.05 mg/ml MIPNP PBS suspension in a 2 ml centrifuge tubes. The centrifuge tubes were agitated in a shaking incubator at 4° C. for 30 min. After adsorption, the peptide or protein concentration in the supernatant was measured. The selectivity test of MIPNPs was also studied in cell culture media. The cell culture media was DMEM with 0.5% of FBS.

Example 1—Preparation and Characterization of MIPNPS

Figure 17A:
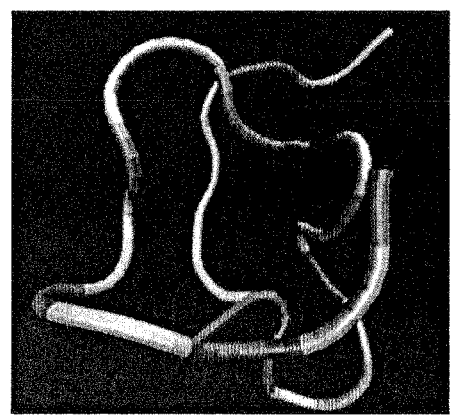
FIGS. 17A and 17B show the amino acid sequence (SEQ ID NO:3) and ribbon structure of ANP (FIG. 17A) and the structure of the template peptide (FIG. 17B).
Figure 17B:
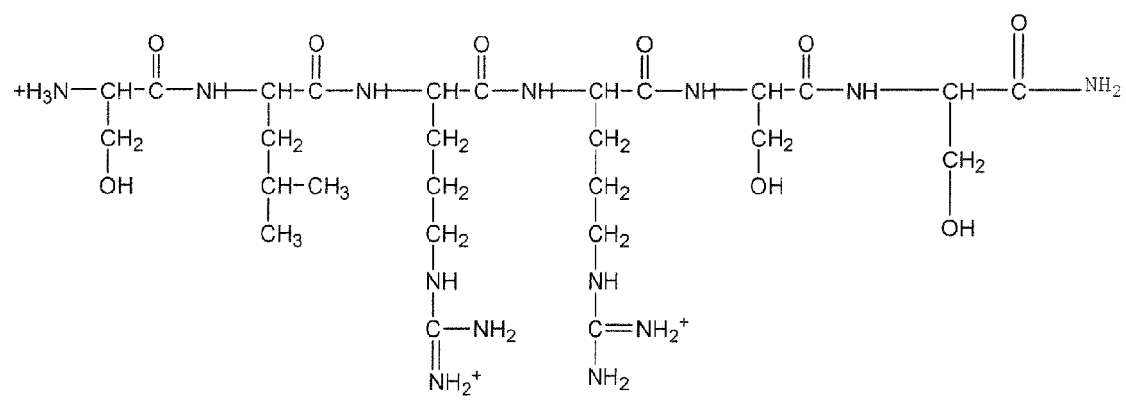

Aqueous molecular imprinting of macromolecules such as peptides and proteins was known to be hindered by steric and thermodynamic effects. It is very difficult for the bulky macromolecules templates moving freely in and out of a polymer matrix [17]. The thermodynamic considerations indicated that the flexible templates yield less well-defined recognition sites in MIP matrix [18]. Recently, the epitope approach has been developed for imprinting proteins and peptides [12, 13, 19]. In this technique, a short peptide from the larger target (as an epitope represents an antigen) is used as a template to create the imprint, which in turn can be used to efficiently recognize both the template and larger target [13]. ANP is a 28-amino acid peptide with a 17-amino acid ring which is formed by a disulfide bond between two cysterine residues at positions 7 and 23 in the middle of the molecule (shown in FIG. 17A). To explore the epitope approach for imprinting ANP, the N-terminus of the peptide ($NH_2$—SLRRSS—$CONH_2$) (SEQ ID NO:2) was chosen as a templating region since it is outside of the ring and has six residues of which three are positively charged, three are polar uncharged (—OH), one is hydrophobic side chain. The monomers used for molecularly imprinted polymer synthesis included methacrylic acid (MAA) and NIPAm as hydrogen bonding, negative charged, and hydrophobic functional monomers, and N,N'-methylenebisacrylamide (BIS) as a cross-linker. The strong electrostatic interactions between the functional monomers and the template molecules will be formed to create molecularly imprinted receptors targeting peptides. FIGS. (1A) and (1B) illustrate the strategy of the epitope approach imprinting ANP and the chemical functions of the imprinting, respectively.

The precipitate polymerization method was employed to prepare MIPNPs at room temperature using water as solvent. BIS was dissolved in the water with the assistant of a little of surfactant SDS. The polymerization was performed with small amount of template (1 μmol) which possesses 3 μmol potential positive charged sites and 1 μmol of the potential hydrophobic site. The inventors employed the functional monomers MAA (3 mM) and NIPAm (1 mM) to template potential sites ratio (1:1000). After studying different ratios of the functional monomers to crosslinking agent (data not shown), the functional monomers MAA and NIPAm to cross-linking agent (BIS) ratio was optimized to 1:3:10. The free radical polymerization was initialized by ammonium persulfate and N,N,N',N'-tetramethylethylenediamine at room temperature. As a weak polycarboxylic acid with pKa=6~7, polymethacrylic acid carried different negative charges at different pH due to different ionization degree of its carboxylic acid groups [20]. When the pH is over pKa, the amount of negative charge is more than that of positive charge. Therefore, the higher electrostatic interaction of functional groups on MIPNPs with the template will be expected when pH is no less than 7. In contrast, when pH is lower than 6, the electrostatic interaction between the MIPNPs and template will be weakened which is helpful to remove the template from the imprinted cavities of the MIPNPs. This pH sensitive adsorption and desorption characteristic is useful for the separation of ANP from the other peptides.

Figure 1B:
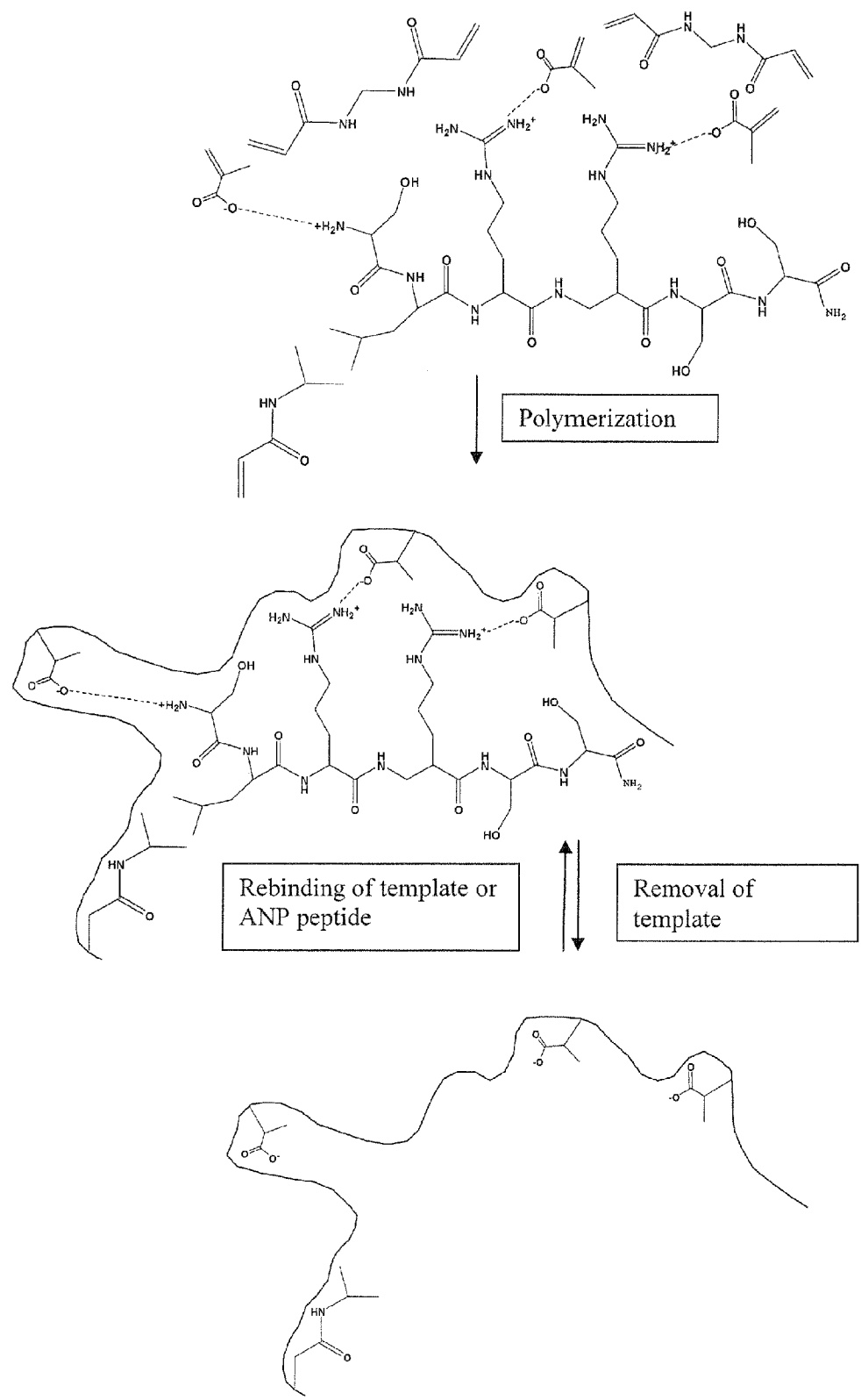
Figure 2A:
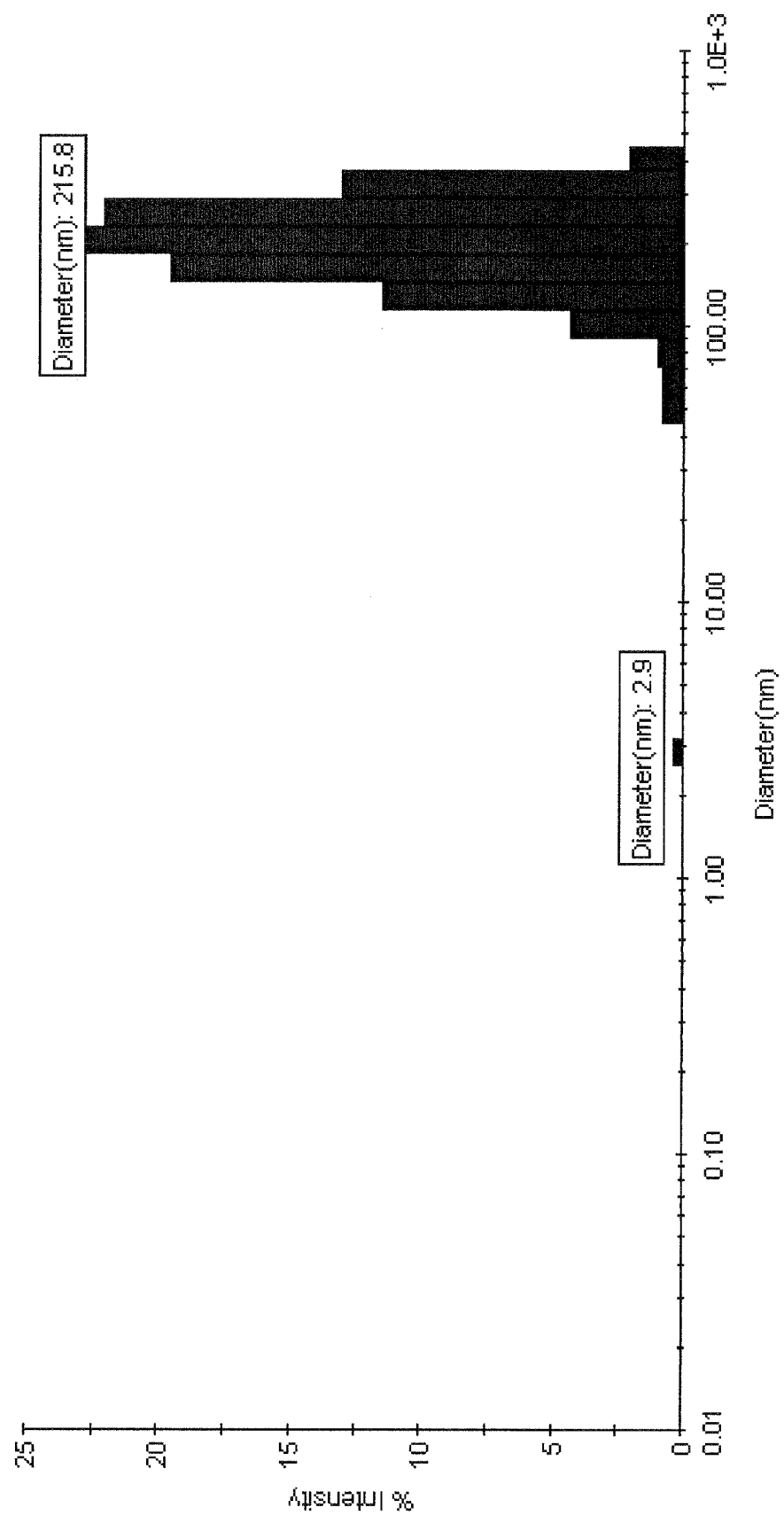
FIGS. 2A and 2B are graphs showing the size distribution of MIPNPs and NIPNPs in water.
Figure 2B:
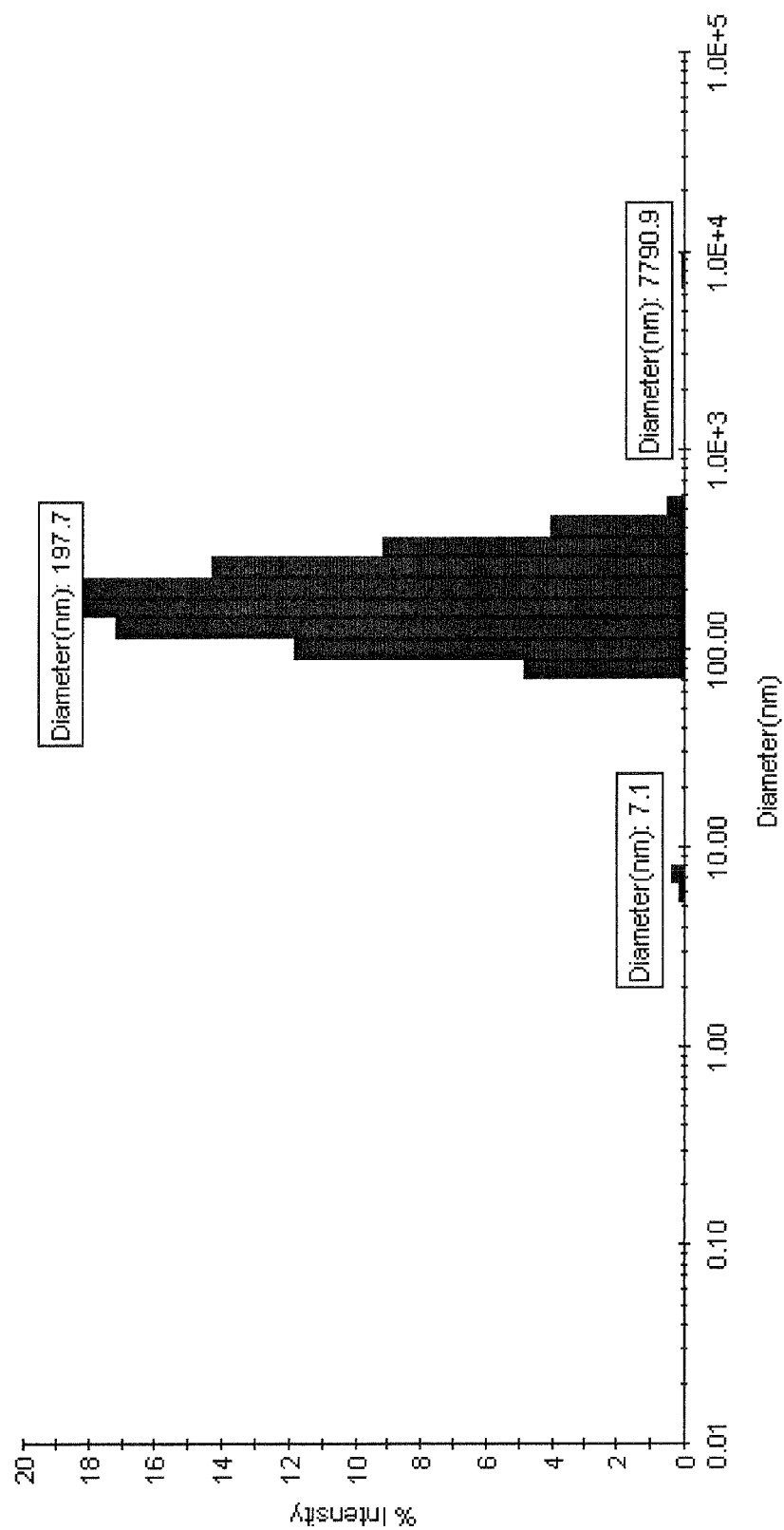

FIGS. 1A and 1B show the hydrodynamic size of the MIPNPs and NIPNPs, characterized by a DynaPro DLS Plate reader. FIGS. 2A and 2B show the particle size distribution of MIPNPs and NIPNPs in water. The average diameter of MIPNPs (215.8±4.6 nm based on 4 times determination) is a little bit larger than NIPNPs (197.7±3.1 nm).

To investigate the affinity of MIPNPs for template peptide and ANP targeting peptide, adsorption isotherm experiments and subsequent Scatchard analysis were carried. The adsorption isotherm of MIPNPs for template peptide was determined in the concentration range of template from 30 to 340 μg/ml. As shown in the FIG. 3, the amount of template peptide bound to the MIPNPs at equilibrium $Q_e$ increased with the increase of the initial concentration of template. The binding capacity of MIPNPs is much higher than NIPNPs. The saturation binding data were further processed with Scatchard equation to estimate the binding properties of MIPs. The Scatchard relationship can be obtained using the following equation.

$$Q_e/C_s = (Q_{max} - Q_e)K_a \quad (3)$$

$Q_{max}$ is the saturated adsorption capacity, $Q_e$ is the amount of protein bound to MIPNPs at equilibrium, $C_s$ is the free concentration after adsorption equilibrium, $K_a$ is the association constant.

Figure 3:
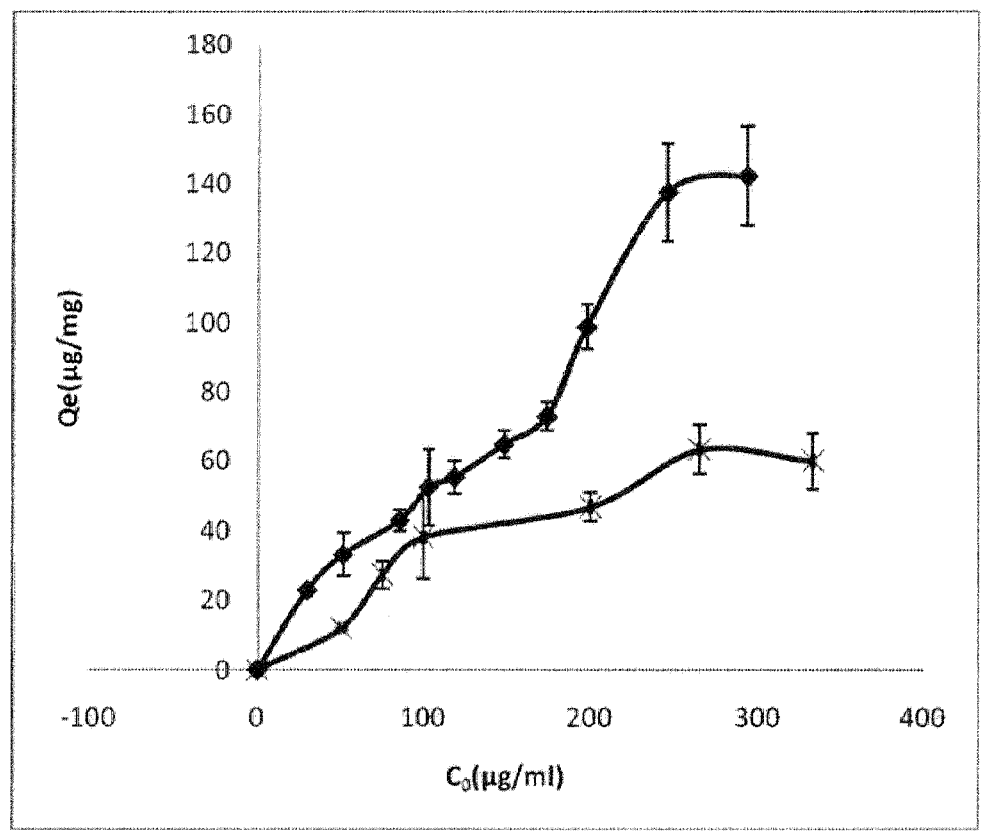
FIG. 3 is a graph showing adsorption isotherm curves ($Q_e$ (mg/g) vs. $C_0$) of MIPNP and NIPNPs for template peptide.
Figure 4:
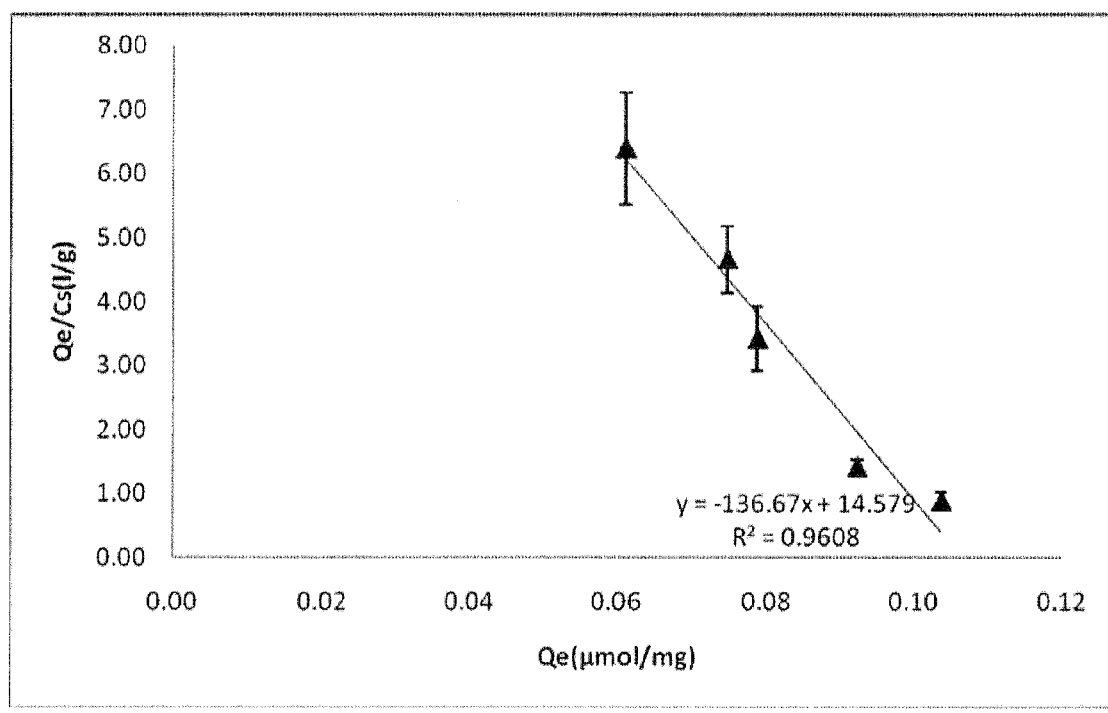
FIG. 4 is a Scatchard plot of MIPNP for template, $Q_e/C_s$ vs. $Q_e$.

FIG. 3 shows the adsorption isotherm curves ($Q_e$ (mg/g) vs. $C_0$) of MIPNP and NIPNPs for template peptide. FIG. 4 is a Scatchard plot of MIPNP for template, $Q_e/C_s$ vs. $Q_e$. By plotting $Q_e/C_s$ versus $Q_e$, the binding association constant Ka and the apparent maximum binding capacity can be calculated from the slope and intercept. The obtained Scatchard plot of MIPNPs for template consisted of one straight line, indicating there is one kind of binding site formed in the MIPNPs. $K_a$ and $Q_{max}$ is $1.36 \times 10^5$ $M^{-1}$ and 86.1 μmol/g respectively.

Figure 5:
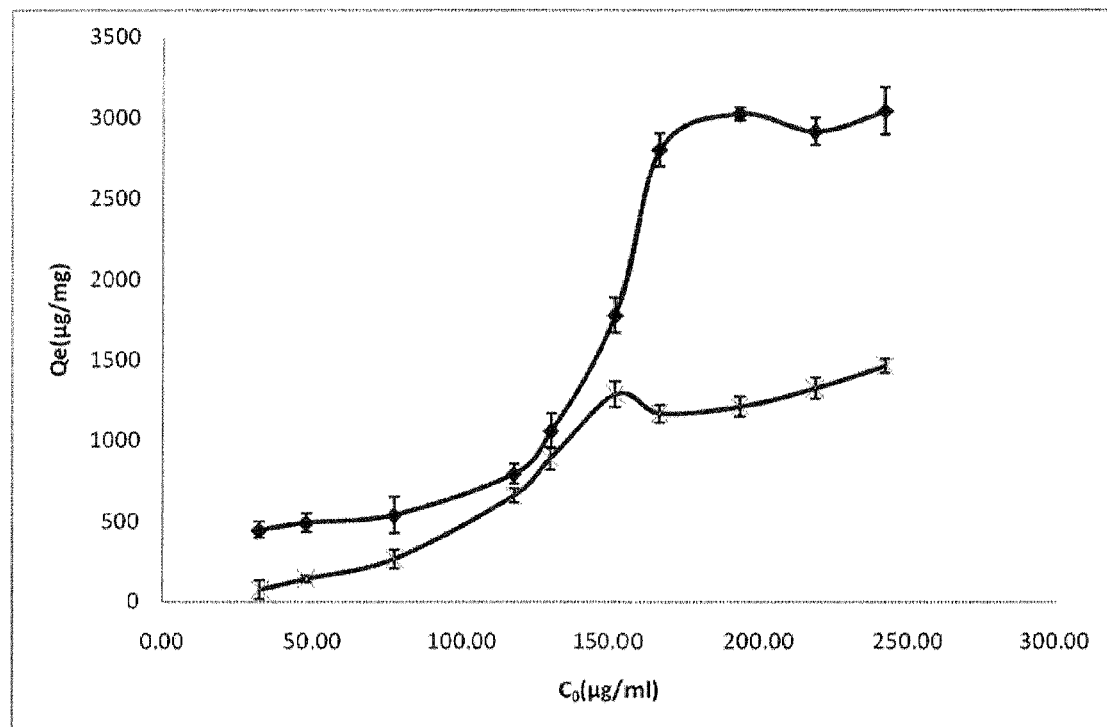
FIG. 5 is a graph showing adsorption isotherm curves (Qe (mg/g) vs $C_0$) of MIPNP and NIPNPs for ANP.
Figure 6:
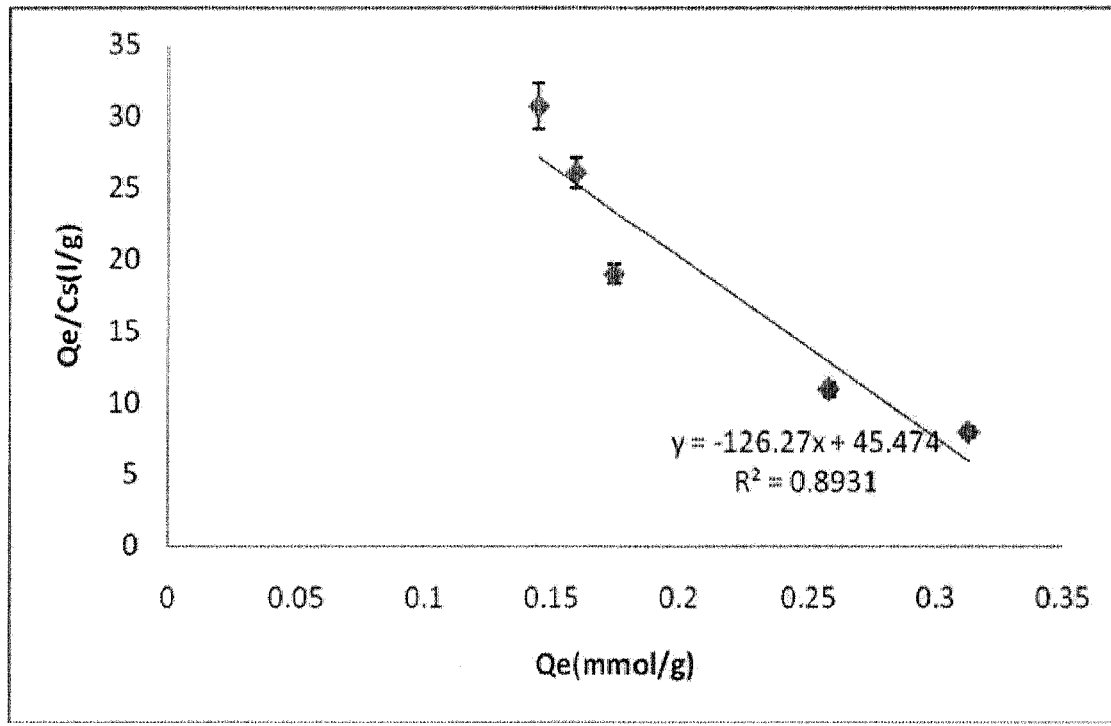
FIG. 6 is a Scatchard curve of MIPNP for ANP ($Q_e/C_s$ vs. $Q_e$).

The adsorption isotherm of MIPNPs for targeting peptide ANP and the following Scatchard analysis were also carried out in the concentration range ANP from 20 to 286 μg/ml. As illustrated in FIG. 5, the adsorption capacity of MIPNPs for ANP also increased with the increase of the concentration of the initial concentration of ANP. Compared to the adsorption capacity of NIPNPs for ANP, the adsorption capacity of MIPNPs is much higher. The Scatchard analysis also gave one straight lines suggesting one kind of binding site present in the MIPNPs. $K_a$ and $Q_{max}$ is $1.26 \times 10^5$ $M^{-1}$ and 0.4 mmol/g, respectively. The binding constant of MIPNPs for target ANP peptide is a little bit lower than that of template peptide.

Figure 7:
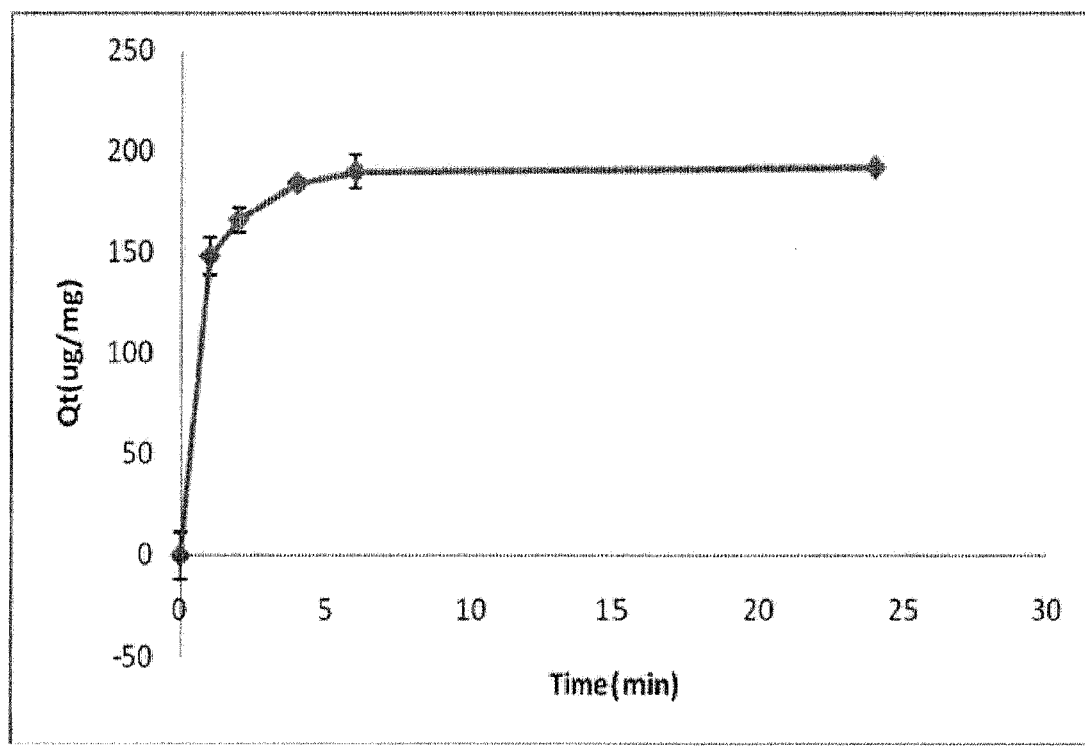
FIG. 7 shows dynamic adsorption profiles of template peptide on MIPNPs, Qt (mg/g) versus time.
Figure 9:
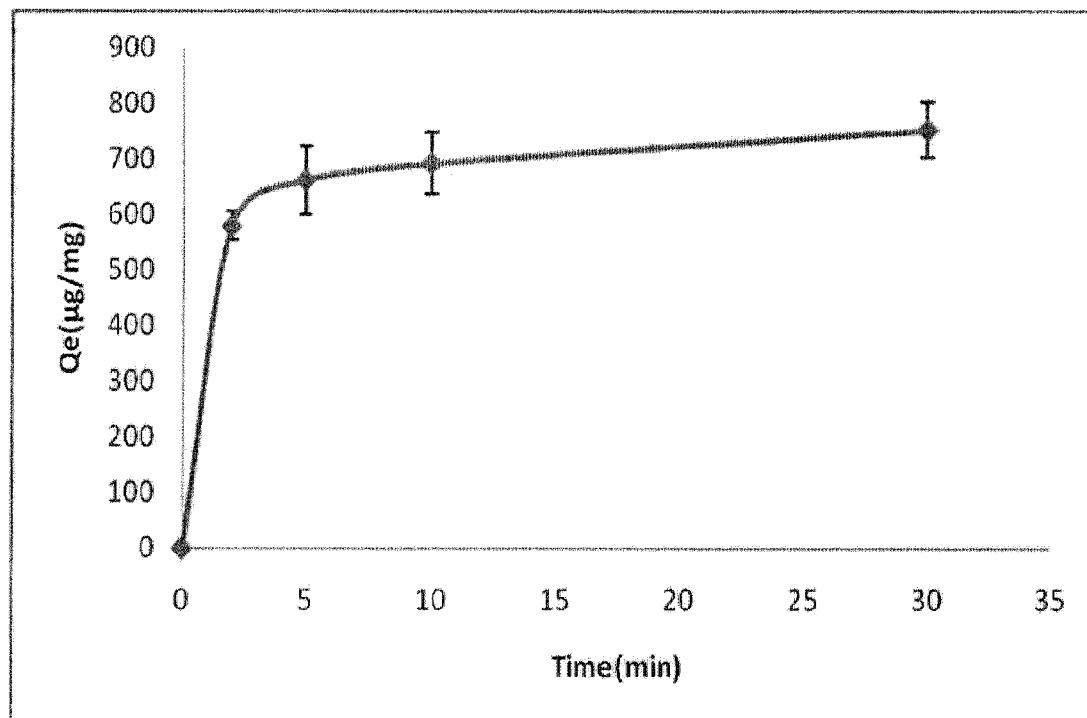
FIG. 9 shows a curve of bound targeting peptide ANP (mg/g) versus time.

The kinetics of the template peptide and targeting peptide binding to the MIPNPs were explored. It took approximately 30 min to reach the adsorption equilibrium of template peptide or ANP peptide on MIPNPs (FIG. 7, FIG. 9). In addition to providing information about how long it will take to reach the binding equilibrium, these experiments provide another way to determine the value of association constants by experimentally measuring the association rate. The first-order rate equation of Lagergren is used for the analysis of the adsorption kinetics of template peptide and targeting peptide on MIPNPs.

$$Ln(Q_e - Q_t)/Q_e = -kt \quad (4) \, [21]$$

Figure 8:
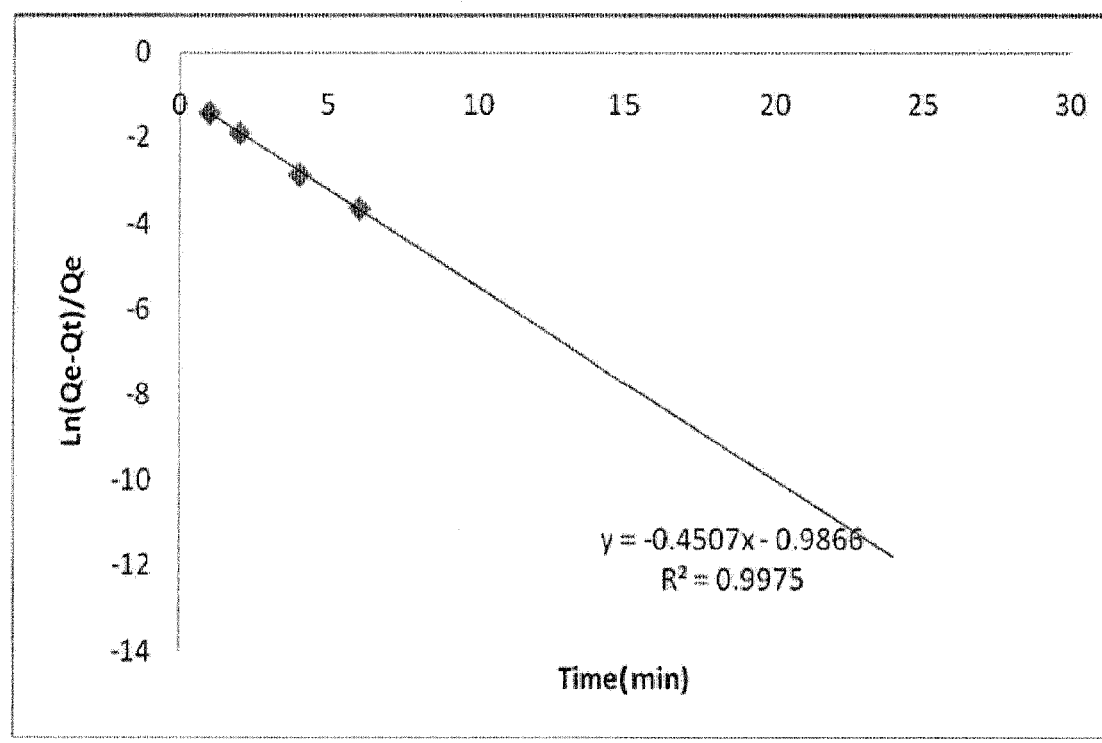
FIG. 8 shows a plot of ln(Qe−Q)/Qe versus time for template peptide.
Figure 10:
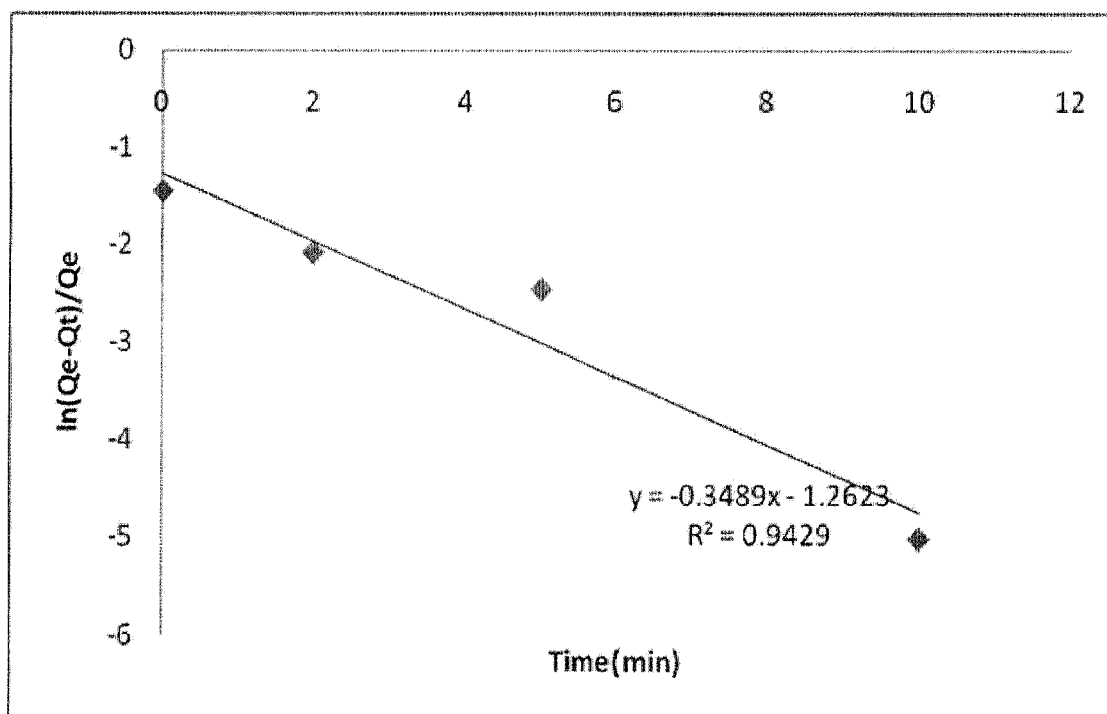
FIG. 10 shows a plot of ln(Qe−Q)/Qe versus time for ANP peptide.

The plots of $ln(Q_e - Q_t)/Q_e$ versus t for template peptide and target peptide gave the linear regressions as shown in FIG. 8 and FIG. 10, respectively. The apparent rate constants characterizing the speed of peptide adsorption were 0.45 for template peptide or 0.35 for target peptide, respectively. The adsorption rate of target peptide onto MIPNPs is slower than that of template peptide. This is reasonable since the size of target peptide is larger than template peptide which results in slower moving rate and orientation rate.

Figure 11:
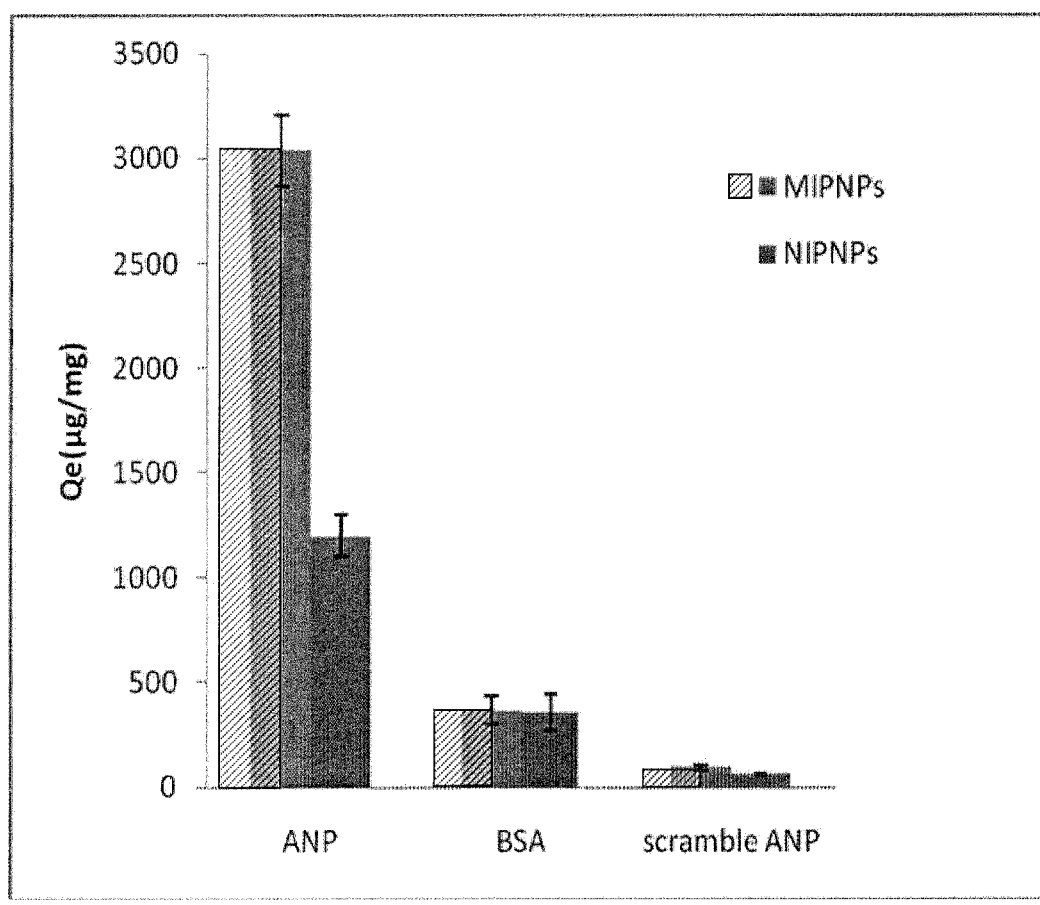
FIGS. 11, 12A and 12B show binding to MIPNPs in a single protein or peptide solution, and ANP binding to MIPNPs or NIPNPs in a cell culture medium. The concentration of each protein or peptide solution initially was 240 μg/ml.
Figure 12A:
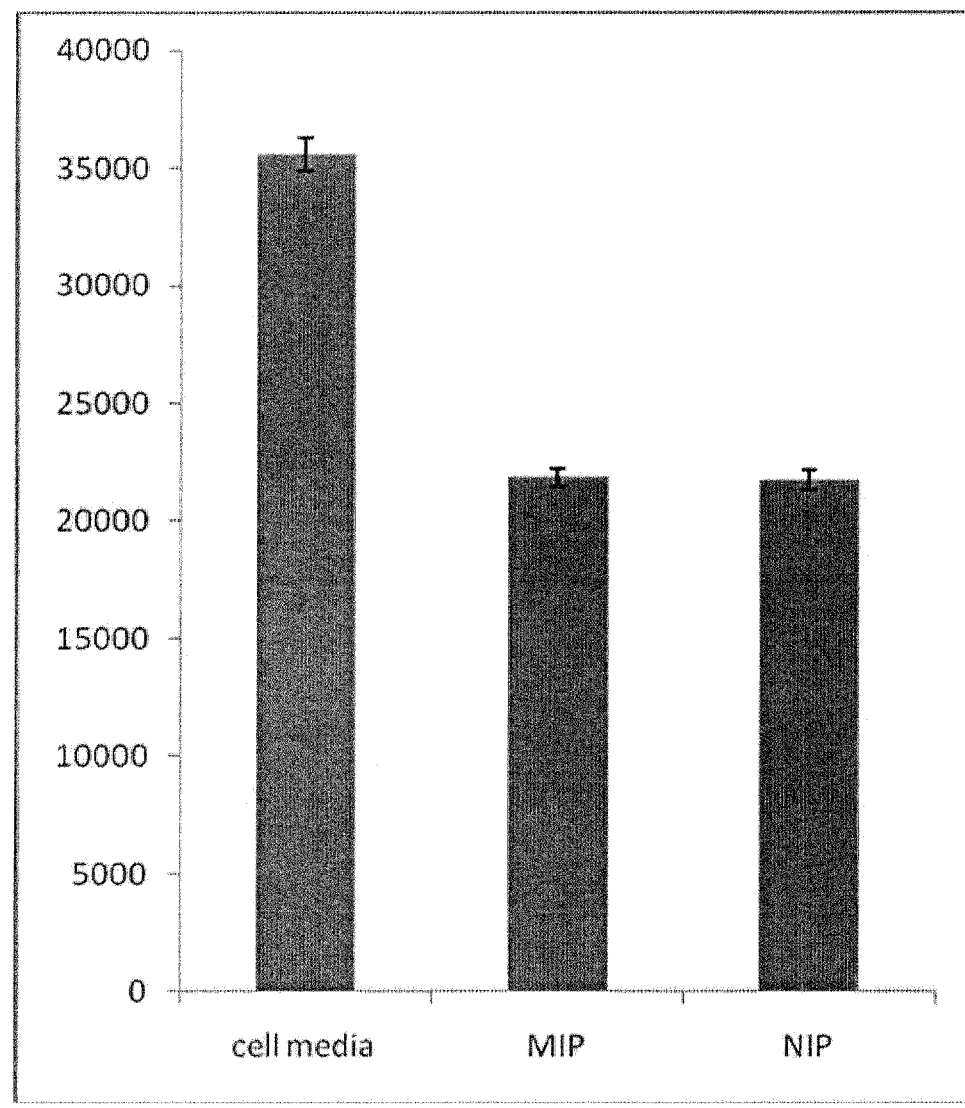
Figure 12B:
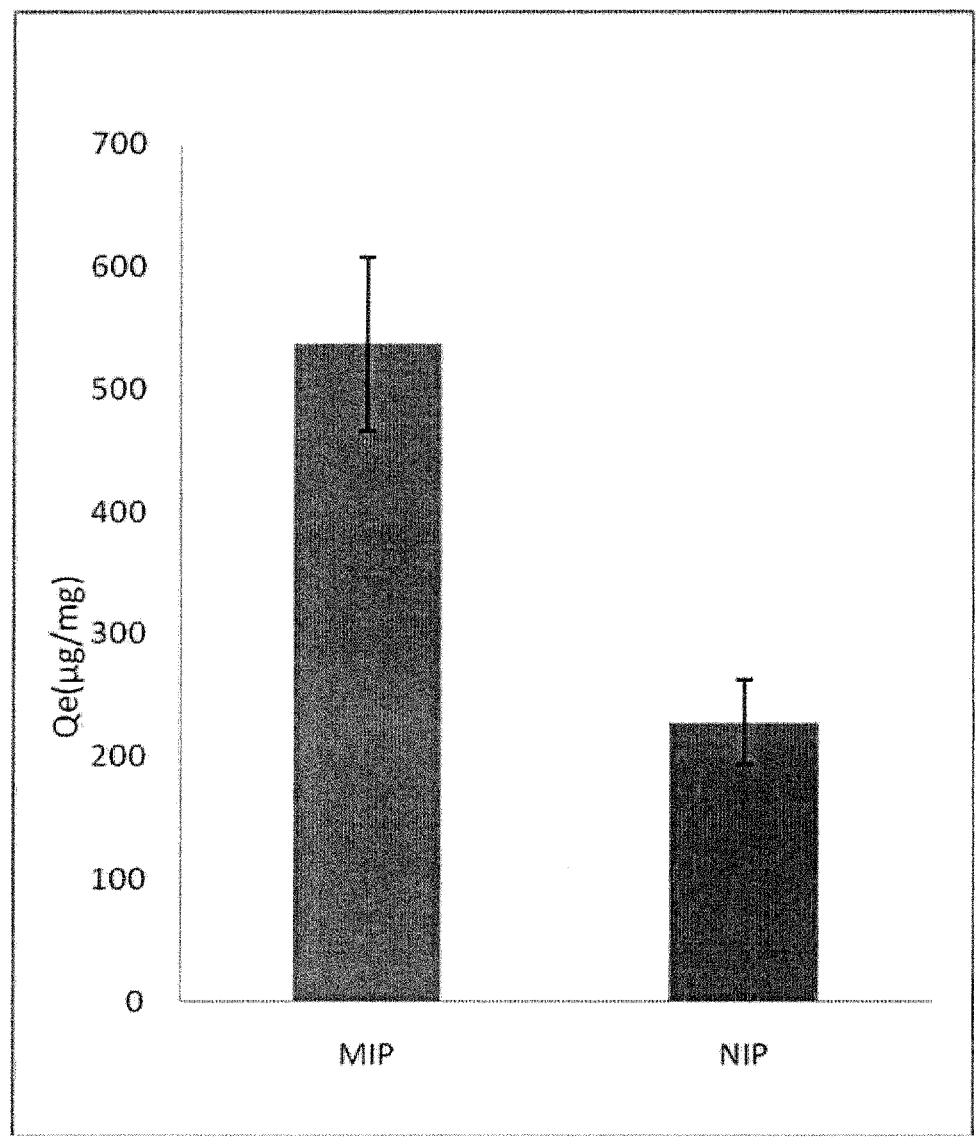
Figure 13:
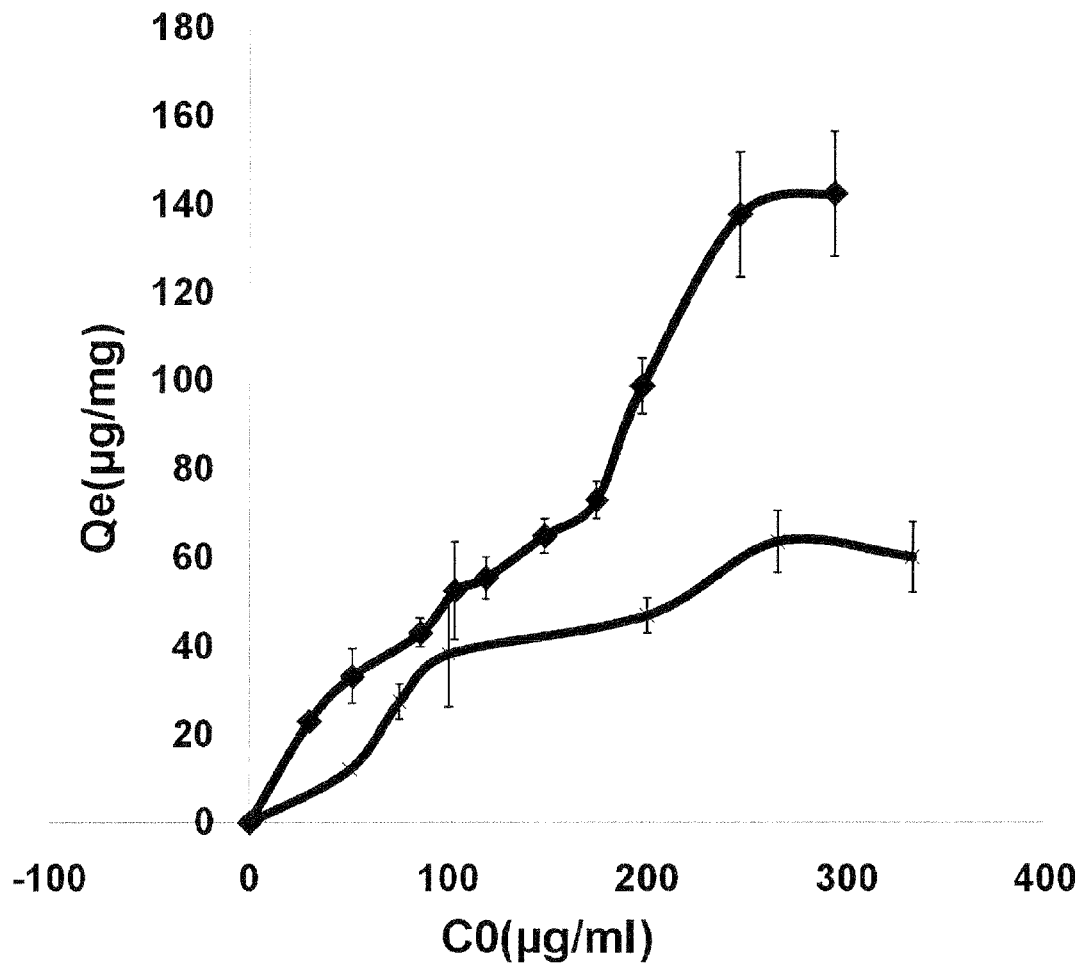
FIG. 13 shows adsorption isotherm curves ($Q_e$ (mg/g) vs. $C_0$) of MIPNP and NIPNPs for template peptide.
Figure 14:
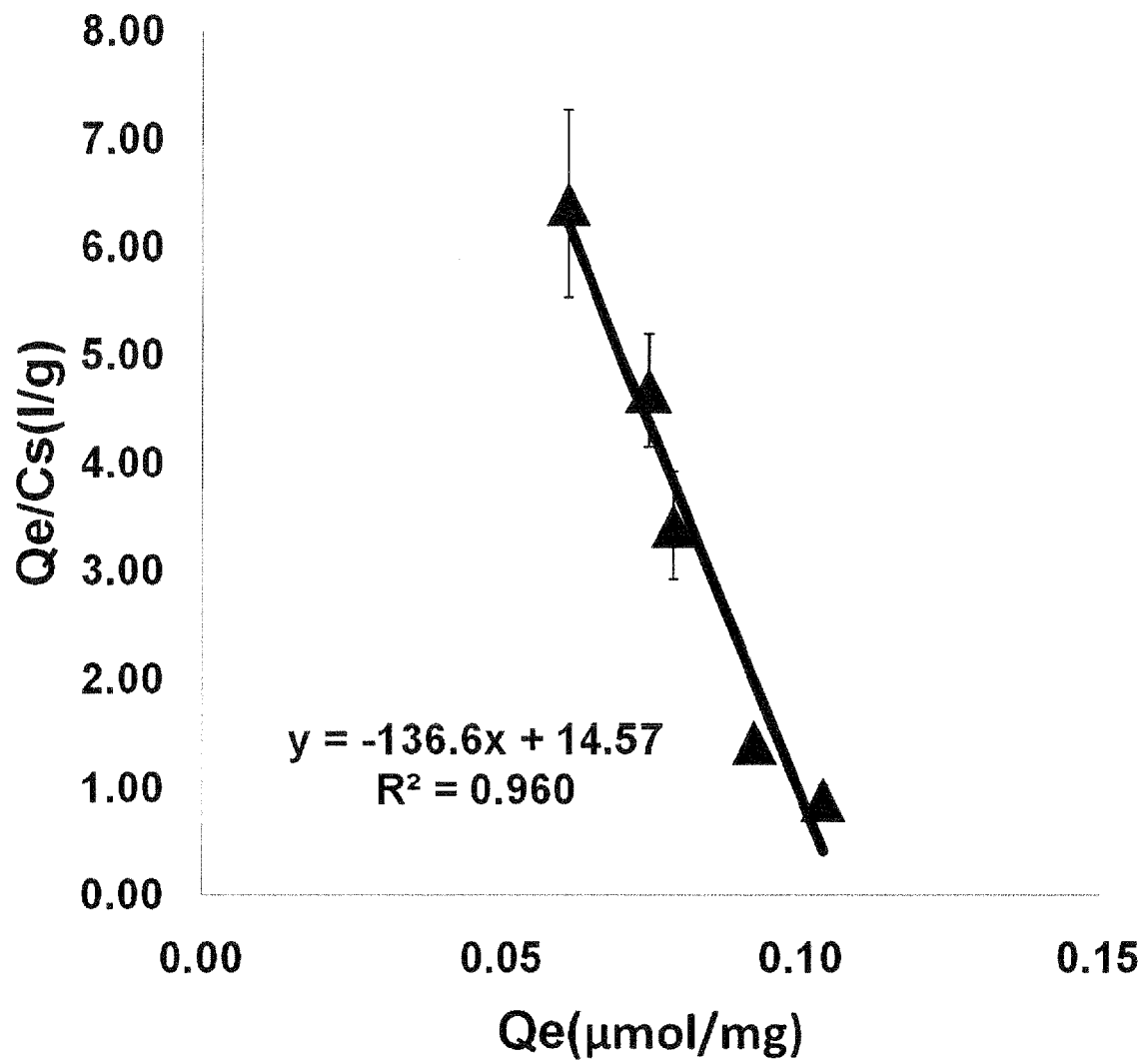
FIG. 14 is a Scatchard plot of MIPNP for template, $Q_e$/Cs vs. $Q_e$.
Figure 15:
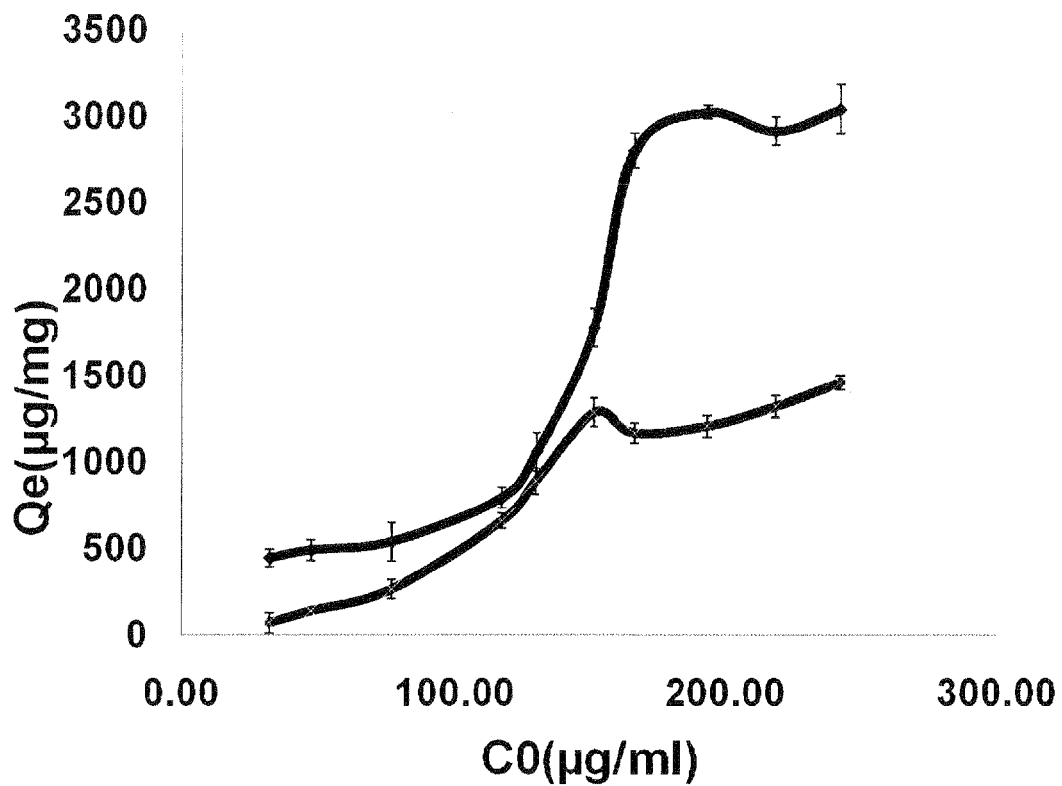
FIG. 15 is a graph showing adsorption isotherm curves ($Q_e$(mg/g) vs $C_0$) of MIPNP and NIPNPs for ANP.
Figure 16:
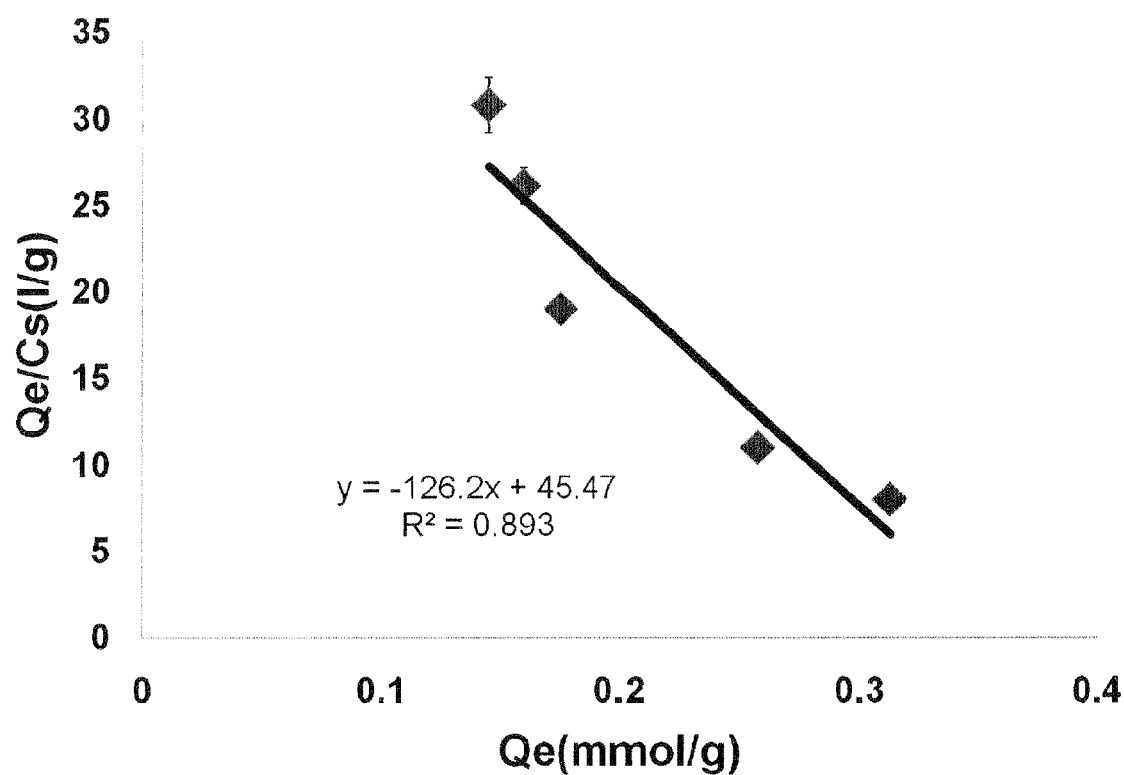
FIG. 16 is a Scatchard Curve of MIPNP for ANP ($Q_e/C_s$ vs. $Q_e$).

The selectivity of MIPNPs compared to the NIPNPs was carried out with the concentration of ANP, scramble ANP and BSA solutions. FIG. 11 demonstrated that MIPNPs have higher binding affinity to ANP, but lack significant affinity to other proteins. Compared to control polymer NIPNPs, MIP-NPs nanoparticles shows excellent affinity to ANP, but not big difference to BSA or scramble ANP.

The plastic antibody ANP (MIPNP) was prepared by precipitate polymerization using an epitope approach. The average diameter of prepared MIPNPs in water was 215.8±4.6 nm which is a little bit higher than NIPNPs 197.7±3.1 nm. According to the binding isotherm results, this MIPNP exhibited a much higher binding ability for the template molecule and ANP than NIPNPs. Scatchard analysis gave the equilibrium binding constant $Ka 1.36 \times 10^5$ $M^{-1}$ with maximum binding capacity 86 μmol/g polymer for template peptide and binding constant $1.26 \times 10^5$ $M^{-1}$ with maximum binding capacity 0.4 mmol/g for target ANP peptide. The binding kinetics studies showed that MIPNPs could easily reach the protein adsorption equilibrium. The results of selectivity demonstrated that MIPNIPs had high affinity to ANP but lacked affinity to BSA or scramble ANP. The prepared synthetic ANP antibody, MIPNP has higher affinity and selectivity to ANP and may be used for modulating ANP-NPR-A signaling.

REFERENCES

[1] Debold A J, Flynn T G. CARDIONATRIN-I—A NOVEL HEART PEPTIDE WITH POTENT DIURETIC AND NATRIURETIC PROPERTIES. *Life Sciences*. 1983; 33:297-302.

[2] Kangawa K, Matsuo H. PURIFICATION AND COMPLETE AMINO-ACID-SEQUENCE OF ALPHA-HUMAN ATRIAL NATRIURETIC POLYPEPTIDE (ALPHA-HANP). *Biochemical and Biophysical Research Communications*. 1984; 118:131-9.

[3] Valsson F, Lundin S, Kirno K, Hedner T, Houltz E, Saito Y, et al. Atrial natriuretic peptide attenuates pacing-induced myocardial ischemia during general anesthesia in patients with coronary artery disease. *Anesthesia and Analgesia*. 1999; 88:279-85.

[4] Kong X, Wang X, Xu W, Behera S, Hellermann G, Kumar A, et al. Natriuretic peptide receptor A as a novel anticancer target. *Cancer Research*. 2008; 68:249-56.

[5] Herman J P, Dolgas C M, Rucker D, Langub M C. Localization of natriuretic peptide-activated guanylate cyclase mRNAs in the rat brain. *Journal of Comparative Neurology*. 1996; 369:165-87.

[6] Goy M F, Oliver P M, Purdy K E, Knowles J W, Fox J E, Mohler P J, et al. Evidence for a novel natriuretic peptide receptor that prefers brain natriuretic peptide over atrial natriuretic peptide. *Biochemical Journal*. 2001; 358: 379-87.

[7] Janiak D S, Kofinas P. Molecular imprinting of peptides and proteins in aqueous media. *Analytical and Bioanalytical Chemistry*. 2007; 389:399-404.

[8] Abbate V, Frascione N, Bansal S S. Preparation, Characterization, and Binding Profile of Molecularly Imprinted Hydrogels for the Peptide Hepeidin. *Journal of Polymer Science Part a-Polymer Chemistry*. 2010; 48:1721-31.

[9] Hart B R, Shea K J. Synthetic peptide receptors: Molecularly imprinted polymers for the recognition of peptides using peptide-metal interactions. *Journal of the American Chemical Society*. 2001; 123:2072-3.

[10] Hart B R, Shea K J. Molecular imprinting for the recognition of N-terminal histidine peptides in aqueous solution. *Macromolecules*. 2002; 35:6192-201.

[11] Hoshino Y, Kodama T, Okahata Y, Shea K J. Peptide Imprinted Polymer Nanoparticles: A Plastic Antibody. *Journal of the American Chemical Society*. 2008; 130: 15242-+.

[12] Rachkov A, Minoura N. Recognition of oxytocin and oxytocin-related peptides in aqueous media using a molecularly imprinted polymer synthesized by the epitope approach. *Journal of Chromatography A*. 2000; 889:111-8.

[13] Rachkov A, Minoura N. Towards molecularly imprinted polymers selective to peptides and proteins. The epitope approach. *Biochimica Et Biophysica Acta-Protein Structure and Molecular Enzymology*. 2001; 1544:255-66.

[14] Hoshino Y, Koide H, Urakami T, Kanazawa H, Kodama T, Oku N, et al. Recognition, Neutralization, and Clearance of Target Peptides in the Bloodstream of Living Mice by Molecularly Imprinted Polymer Nanoparticles: A Plastic Antibody. *Journal of the American Chemical Society*. 2010; 132:6644-+.

[15] Hoshino Y, Urakami T, Kodama T, Koide H, Oku N, Okahata Y, et al. Design of Synthetic Polymer Nanoparticles that Capture and Neutralize a Toxic Peptide. *Small*. 2009; 5:1562-8.

[16] Lin C Y, Tai D F, Wu T Z. Discrimination of peptides by using a molecularly imprinted piezoelectric biosensor. *Chemistry—a European Journal*. 2003; 9:5107-10.

[17] Flam F. MOLECULAR IMPRINTS MAKE A MARK. *Science*. 1994; 263:1221-2.

[18] Nicholls I A. THERMODYNAMIC CONSIDERATIONS FOR THE DESIGN OF AND LIGAND RECOGNITION BY MOLECULARLY IMPRINTED POLYMERS. *Chemistry Letters*. 1995:1035-6.

[19] Nishino H, Huang C S, Shea K J. Selective protein capture by epitope imprinting. *Angewandte Chemie-International Edition*. 2006; 45:2392-6.

[20] Guo W, Hu N F. Interaction of myoglobin with poly (methacrylic acid) at different pH in their layer-by-layer assembly films: An electrochemical study. *Biophysical Chemistry*. 2007; 129:163-71.

[21] Li L, He X W, Chen L X, Zhang Y K. Preparation of novel bovine hemoglobin surface-imprinted polystyrene nanoparticles with magnetic susceptibility. *Science in China Series B-Chemistry*. 2009; 52:1402-11.

[22] Potter L R, et al. *Endocrine Reviews*. 2006; 27(1):47-72.

[23] Lee C Y, et al. *J. Investig. Med.* 2009; 57(1):18-21.

[24] Ferris and Missbichler. Construction and use of two α-human atrial natriuretic peptide-fragment affinity chromatography columns in the isolation of C- and N-terminal epitope-specific antibodies for use in a prototype α-hANP biosensor. *Journal of Chromatography*. 1992; 577:251-265.

[25] Zhang et al. Plasmid-encoded NP73-102 modulates atrial natriuretic peptide receptor signaling and plays a critical role in inducing terologenic dendritic cells. *Genetic Vaccines and Therapy*. 2011; 9(3):1-12.

[26] Kong et al. Natriuretic Peptide Receptor A as a Novel Anticancer Target. *Cancer Research*. 2008; 68:249-256.

[27] Kandasamy et al. Isatin down-regulates expression of atrial natiuretic peptide receptor-A and inhibits airway inflammation in a mouse model of allergic asthma. *International Immunopharmacology*. 2010; 10:218-225.

[28] Hoshino et al. Design of Synthetic Polymer Nanoparticles that Capture and Neutralize a Toxic Peptide. *Small.* 2009 July; 5(13):1562-1568.

[29] Hoshino et al. The rational design of a synthetic polymer nanoparticle that neutralizes a toxic peptide in vivo. *PNAS,* 2012 January; 109(1):33-38.

[30] Hoshino et al. Recognition, neutralization and clearance of target peptides in the blood stream of living mice by molecular imprinted polymer nanoparticles: a plastic antibody. *J Am Chem Soc.,* 2010 May; 132(19):6644-6645.

[31] WO 2010/081076 (Hoshino et al., published Jul. 15, 2010).

What is claimed is:

1. A composition of matter, comprising a molecularly imprinted polymer (MIP) nanoparticle having binding affinity for an atrial natriuretic peptide comprising amino acid sequence SLRRSSCFGGRMDRIGAQSGLGCNSFRY (SEQ ID NO: 3), wherein the MIP nanoparticle comprises; (i) methacrylic acid (MAA), N-isopropylacrylamide (NIPAm), and N, N'-methylenebisacrylamide (BIS) in a molar ratio of MMA:NIPAm:BIS of 1:3:10, and (ii) an imprint that possesses steric and chemical memory for amino acid sequence SLRRSS (SEQ ID NO: 2) of the atrial natriuretic peptide, and wherein the MIP nanoparticle selectively binds to SEQ ID NO: 2 of the atrial natriuretic peptide comprising amino acid SEQ ID NO: 3.

2. The composition of matter of claim 1, wherein the composition of matter is a pharmaceutical composition comprising one or more of the MIP nanoparticles and a pharmaceutically acceptable carrier.

3. The composition of matter of claim 1, wherein the MIP nanoparticle further comprises a detectable moiety associated with the MIP nanoparticle.

* * * * *

UNITED STATES PATENT AND TRADEMARK OFFICE
CERTIFICATE OF CORRECTION

PATENT NO. : 9,695,262 B2
APPLICATION NO. : 14/000326
DATED : July 4, 2017
INVENTOR(S) : Subhra Mohapatra and Chunyan Wang Page 1 of 1

It is certified that error appears in the above-identified patent and that said Letters Patent is hereby corrected as shown below:

<u>Column 5,</u>
Lines 19-20, "10 mol/g" should read --10 µmol/g--.

<u>Column 9,</u>
Line 58, "86 mol/g" should read --86 µmol/g--.

Signed and Sealed this
Twenty-first Day of August, 2018

Andrei Iancu
*Director of the United States Patent and Trademark Office*

SEQUENCE LISTING

```
<160> NUMBER OF SEQ ID NOS: 14

<210> SEQ ID NO 1
<211> LENGTH: 4
<212> TYPE: PRT
<213> ORGANISM: ARTIFICIAL SEQUENCE
<220> FEATURE:
<223> OTHER INFORMATION: Oxytocin-related peptide

<400> SEQUENCE: 1

Tyr Pro Leu Gly
1

<210> SEQ ID NO 2
<211> LENGTH: 6
<212> TYPE: PRT
<213> ORGANISM: ARTIFICIAL SEQUENCE
<220> FEATURE:
<223> OTHER INFORMATION: Amine-terminal ANP

<400> SEQUENCE: 2

Ser Leu Arg Arg Ser Ser
1               5

<210> SEQ ID NO 3
<211> LENGTH: 28
<212> TYPE: PRT
<213> ORGANISM: Homo sapiens

<400> SEQUENCE: 3

Ser Leu Arg Arg Ser Ser Cys Phe Gly Gly Arg Met Asp Arg Ile Gly
1               5                   10                  15

Ala Gln Ser Gly Leu Gly Cys Asn Ser Phe Arg Tyr
            20                  25

<210> SEQ ID NO 4
<211> LENGTH: 32
<212> TYPE: PRT
<213> ORGANISM: Homo sapiens

<400> SEQUENCE: 4

Ser Pro Lys Met Val Gln Gly Ser Gly Cys Phe Gly Arg Lys Met Asp
1               5                   10                  15

Arg Ile Ser Ser Ser Ser Gly Leu Gly Cys Lys Val Leu Arg Arg His
            20                  25                  30

<210> SEQ ID NO 5
<211> LENGTH: 29
<212> TYPE: PRT
<213> ORGANISM: Homo sapiens

<400> SEQUENCE: 5

Tyr Lys Gly Ala Asn Lys Lys Gly Leu Ser Lys Gly Cys Phe Gly Leu
1               5                   10                  15

Lys Leu Asp Arg Ile Gly Ser Met Ser Gly Leu Gly Cys
            20                  25
```

<210> SEQ ID NO 6
<211> LENGTH: 32
<212> TYPE: PRT
<213> ORGANISM: Homo sapiens

<400> SEQUENCE: 6

Asn Leu Gly His Gly Leu Tyr Pro Asp Met Asp Pro Glu His Val Gly
 1               5                  10                  15

Ala Phe Val Asp Ala Val His Lys His Ser Arg Leu Leu Arg Gln Asn
            20                  25                  30

<210> SEQ ID NO 7
<211> LENGTH: 30
<212> TYPE: PRT
<213> ORGANISM: Homo sapiens

<400> SEQUENCE: 7

Asn Pro Met Tyr Asn Ala Val Ser Asn Ala Asp Leu Met Asp Phe Lys
 1               5                  10                  15

Asn Leu Leu Asp His Leu Glu Glu Lys Met Pro Leu Glu Asp
            20                  25                  30

<210> SEQ ID NO 8
<211> LENGTH: 37
<212> TYPE: PRT
<213> ORGANISM: Homo sapiens

<400> SEQUENCE: 8

Glu Val Val Pro Pro Gln Val Leu Ser Glu Pro Asn Glu Glu Ala Gly
 1               5                  10                  15

Ala Ala Leu Ser Pro Leu Pro Glu Val Pro Pro Trp Thr Gly Glu Val
            20                  25                  30

Ser Pro Ala Gln Arg
        35

<210> SEQ ID NO 9
<211> LENGTH: 20
<212> TYPE: PRT
<213> ORGANISM: Homo sapiens

<400> SEQUENCE: 9

Ser Ser Asp Arg Ser Ala Leu Leu Lys Ser Lys Leu Arg Ala Leu Leu
 1               5                  10                  15

Thr Ala Pro Arg
        20

<210> SEQ ID NO 10
<211> LENGTH: 30
<212> TYPE: PRT
<213> ORGANISM: Homo sapiens

<400> SEQUENCE: 10

Gly Arg Gly Pro Trp Asp Ser Ser Asp Arg Ser Ala Leu Leu Lys Ser
 1               5                  10                  15

Lys Leu Arg Ala Leu Leu Thr Ala Pro Arg Ser Leu Arg Arg
            20                  25                  30

<210> SEQ ID NO 11
<211> LENGTH: 38
<212> TYPE: PRT
<213> ORGANISM: Dendroaspis angusticeps

<400> SEQUENCE: 11

```
Glu Val Lys Tyr Asp Pro Cys Phe Gly His Lys Ile Asp Arg Ile Asn
1               5                   10                  15

His Val Ser Asn Leu Gly Cys Pro Ser Leu Arg Asp Pro Arg Pro Asn
            20                  25                  30

Ala Pro Ser Thr Ser Ala
        35

<210> SEQ ID NO 12
<211> LENGTH: 17
<212> TYPE: PRT
<213> ORGANISM: ARTIFICIAL SEQUENCE
<220> FEATURE:
<223> OTHER INFORMATION: conserved sequence of natriuretic peptides
<220> FEATURE:
<221> NAME/KEY: misc_feature
<222> LOCATION: (4)..(6)
<223> OTHER INFORMATION: Xaa can be any naturally occurring amino acid
<220> FEATURE:
<221> NAME/KEY: misc_feature
<222> LOCATION: (10)..(13)
<223> OTHER INFORMATION: Xaa can be any naturally occurring amino acid

<400> SEQUENCE: 12

Cys Phe Gly Xaa Xaa Xaa Asp Arg Ile Xaa Xaa Xaa Xaa Gly Leu Gly
1               5                   10                  15

Cys

<210> SEQ ID NO 13
<211> LENGTH: 17
<212> TYPE: PRT
<213> ORGANISM: ARTIFICIAL SEQUENCE
<220> FEATURE:
<223> OTHER INFORMATION: conserved sequence of natriuretic peptides
<220> FEATURE:
<221> NAME/KEY: misc_feature
<222> LOCATION: (4)..(6)
<223> OTHER INFORMATION: Xaa can be any naturally occurring amino acid
<220> FEATURE:
<221> NAME/KEY: misc_feature
<222> LOCATION: (10)..(13)
<223> OTHER INFORMATION: Xaa can be any naturally occurring amino acid
<220> FEATURE:
<221> NAME/KEY: MISC_FEATURE
<222> LOCATION: (14)..(14)
<223> OTHER INFORMATION: Xaa can be Gly or Asn

<400> SEQUENCE: 13

Cys Phe Gly Xaa Xaa Xaa Asp Arg Ile Xaa Xaa Xaa Xaa Leu Gly
1               5                   10                  15

Cys

<210> SEQ ID NO 14
<211> LENGTH: 17
<212> TYPE: PRT
<213> ORGANISM: ARTIFICIAL SEQUENCE
<220> FEATURE:
<223> OTHER INFORMATION: conserved sequence of natriuretic peptides
<220> FEATURE:
<221> NAME/KEY: misc_feature
<222> LOCATION: (4)..(6)
<223> OTHER INFORMATION: Xaa can be any naturally occurring amino acid
<220> FEATURE:
<221> NAME/KEY: misc_feature
<222> LOCATION: (10)..(12)
<223> OTHER INFORMATION: Xaa can be any naturally occurring amino acid

<400> SEQUENCE: 14

Cys Phe Gly Xaa Xaa Xaa Asp Arg Ile Xaa Xaa Xaa Ser Gly Leu Gly
```

-continued

```
1               5               10              15
Cys
```